(12) United States Patent
Lu et al.

(10) Patent No.: US 9,968,579 B2
(45) Date of Patent: May 15, 2018

(54) ATRA FOR MODULATING PIN1 ACTIVITY AND STABILITY

(71) Applicant: Beth Israel Deaconess Medical Center, Inc., Boston, MA (US)

(72) Inventors: Kun Ping Lu, Newton, MA (US); Xiao Zhen Zhou, Newton, MA (US); Shuo Wei, Chestnut Hill, MA (US)

(73) Assignee: Beth Isreal Deaconess Medical Center, Inc., Boston, MA (US)

( * ) Notice: Subject to any disclaimer, the term of this patent is extended or adjusted under 35 U.S.C. 154(b) by 0 days. days.

(21) Appl. No.: 15/326,979

(22) PCT Filed: Jul. 16, 2015

(86) PCT No.: PCT/US2015/040774
§ 371 (c)(1),
(2) Date: Jan. 17, 2017

(87) PCT Pub. No.: WO2016/011268
PCT Pub. Date: Jan. 21, 2016

(65) Prior Publication Data
US 2017/0202799 A1 Jul. 20, 2017

Related U.S. Application Data

(60) Provisional application No. 62/025,577, filed on Jul. 17, 2014.

(51) Int. Cl.
| A61K 31/203 | (2006.01) |
| A61K 45/06 | (2006.01) |
| A61K 31/122 | (2006.01) |
| A61K 31/192 | (2006.01) |
| A61K 31/428 | (2006.01) |
| A61K 31/353 | (2006.01) |

(52) U.S. Cl.
CPC .......... *A61K 31/203* (2013.01); *A61K 31/122* (2013.01); *A61K 31/192* (2013.01); *A61K 31/353* (2013.01); *A61K 31/428* (2013.01); *A61K 45/06* (2013.01)

(58) Field of Classification Search
CPC .................................................... A61K 31/203
USPC ......................................................... 514/367
See application file for complete search history.

(56) References Cited

U.S. PATENT DOCUMENTS

| 4,683,195 A | 7/1987 | Mullis et al. |
| 4,683,202 A | 7/1987 | Mullis |
| 5,223,409 A | 6/1993 | Ladner et al. |
| 5,283,317 A | 2/1994 | Saifer et al. |
| 5,952,467 A | 9/1999 | Hunter et al. |
| 5,972,697 A | 10/1999 | Hunter et al. |
| 6,462,173 B1 | 10/2002 | Lu et al. |
| 6,495,376 B1 | 12/2002 | Lu et al. |
| 6,596,848 B1 | 7/2003 | Hunter et al. |
| 6,764,698 B1 | 7/2004 | Byun et al. |
| 7,125,677 B2 | 10/2006 | Hunter et al. |
| 7,125,955 B2 | 10/2006 | Hunter et al. |
| 7,148,003 B2 | 12/2006 | Hunter et al. |
| 7,161,060 B1 | 1/2007 | Duff et al. |
| 7,164,012 B2 | 1/2007 | Hunter et al. |
| 7,175,830 B2 | 2/2007 | Collins et al. |
| 8,129,131 B2 | 3/2012 | Lu et al. |
| 8,258,099 B2 | 9/2012 | Lu et al. |
| 2002/0025521 A1 | 2/2002 | Lu et al. |
| 2002/0106348 A1 | 8/2002 | Huang et al. |
| 2004/0176912 A1 | 9/2004 | Sowadski et al. |
| 2005/0159485 A1 | 7/2005 | Jost-Price et al. |
| 2006/0018899 A1 | 1/2006 | Kao et al. |
| 2006/0074222 A1 | 4/2006 | Lu et al. |
| 2008/0118505 A1 | 5/2008 | Tedder |
| 2008/0214470 A1 | 9/2008 | Lu et al. |
| 2008/0248043 A1 | 10/2008 | Babcook et al. |

(Continued)

FOREIGN PATENT DOCUMENTS

| WO | WO-94/10300 A1 | 5/1994 |
| WO | WO-97/17986 A1 | 5/1997 |

(Continued)

OTHER PUBLICATIONS

U.S. Appl. No. 61/968,862, Lu et al.
Arrieta et al., "Randomized phase II trial of All-trans-retinoic acid with chemotherapy based on paclitaxel and cisplatin as first-line treatment in patients with advanced non-small-cell lung cancer," J Clin Oncol. 28(21):3463-71 (2010).
Bao et al., "Prevalent overexpression of prolyl isomerase Pin1 in human cancers," Am J Pathol. 164(5):1727-37 (2004).
Bartkova et al., "Cyclin D1 protein expression and function in human breast cancer," Int J Cancer. 57(3):353-61 (1994).
Budd et al., "Phase I/II trial of all-trans retinoic acid and tamoxifen in patients with advanced breast cancer," Clin Cancer Res. 4(3):635-42 (1998).
Connolly et al., "Molecular pathways: current role and future directions of the retinoic acid pathway in cancer prevention and treatment," Clin Cancer Res. 19(7):1651-9 (2013).
Decensi et al., "Randomized double-blind 2 x 2 trial of low-dose tamoxifen and fenretinide for breast cancer prevention in high-risk premenopausal women," J Clin Oncol. 27(23):3749-56 (2009).
Esnault et al., "Pin1 modulates the type 1 immune response," PLoS One. 2(2):e226 (2007) (9 pages).

(Continued)

Primary Examiner — Taofiq A Solola
(74) Attorney, Agent, or Firm — Clark & Elbing LLP

(57) ABSTRACT

The present disclosure describes how all-retinoic acid (ATRA) binds and inhibits Pin1 activity and induces degradation of the activated Pin1 monomer selectively in cancer cells. Identification of the binding mechanism of ATRA with Pin1 confirm ATRA binding specificity to Pin1 residues in the PPIase active site, thus demonstrating that drug-induced Pin1 ablation has potent anticancer activity, such as in acute promyelocytic leukemia (APL), by inducing PML-RARa degradation, as well as against other types of cancer and diseases that are associated with Pin1 overexpression, such as aggressive triple negative breast cancer, lupus, asthma, cocaine addiction, among others, due to their unique ability to simultaneously block numerous cancer-driving pathways, with relatively lower toxicity. The present disclosure also provides a rationale for developing sustained released ATRA-containing formulations. ATRA-containing formulations may be used in combinations with other existing therapies including chemotherapy or molecularly targeted drugs and other standard of care.

19 Claims, 14 Drawing Sheets

(56) References Cited

U.S. PATENT DOCUMENTS

| | | |
|---|---|---|
| 2009/0318391 A1 | 12/2009 | Ben-Sasson |
| 2010/0010084 A1 | 1/2010 | Yu |
| 2010/0278832 A1 | 11/2010 | Kamogawa et al. |
| 2011/0104756 A1 | 5/2011 | Rodriguez et al. |
| 2012/0183560 A1 | 7/2012 | Akassoglou |
| 2013/0028900 A1 | 1/2013 | Lu et al. |
| 2014/0086909 A1 | 3/2014 | Lu et al. |
| 2014/0219957 A1 | 8/2014 | Lu et al. |
| 2014/0242100 A1 | 8/2014 | Lu et al. |
| 2015/0044278 A1 | 2/2015 | Lu et al. |

FOREIGN PATENT DOCUMENTS

| | | |
|---|---|---|
| WO | WO-99/09969 A1 | 3/1999 |
| WO | WO-02/065091 A2 | 8/2002 |
| WO | WO-02/092765 A2 | 11/2002 |
| WO | WO-2004/016751 A2 | 2/2004 |
| WO | WO-2004/101745 A2 | 11/2004 |
| WO | WO-2005/027727 A2 | 3/2005 |
| WO | WO-2005/105058 A1 | 11/2005 |
| WO | WO-2009/003096 A2 | 12/2008 |
| WO | WO-2009/146218 A2 | 12/2009 |
| WO | WO-2012/125724 A1 | 9/2012 |
| WO | WO-2013/185055 A1 | 12/2013 |
| WO | WO-2014/152157 A2 | 9/2014 |
| WO | WO-2016/011268 A1 | 1/2016 |

OTHER PUBLICATIONS

Gianni et al., "Inhibition of the peptidyl-prolyl-isomerase Pin1 enhances the responses of acute myeloid leukemia cells to retinoic acid via stabilization of RARalpha and PML-RARalpha," Cancer Res. 69(3):1016-26 (2009).

Gillet et al., "Amplification and overexpression of cyclin D1 in breast cancer detected by immunohistochemical staining," Cancer Res. 54(7):1812-7 (1994).

Hu et al., "Nanoparticle-assisted combination therapies for effective cancer treatment," Ther Deliv. 1(2):323-34 (2010).

International Preliminary Report on Patentability for International Application No. PCT/US12/029077, dated Sep. 17, 2013 (6 pages).

International Preliminary Report on Patentability for International Application No. PCT/US15/040774, dated Jan. 17, 2017 (6 pages).

International Search Report and Written Opinion for International Application No. PCT/US14/27017, dated Oct. 28, 2014 (19 pages).

International Search Report and Written Opinion for International Application No. PCT/US15/40774, dated Oct. 23, 2015 (13 pages).

International Search Report and Written Opinion for International Application No. PCT/US2012/029077, dated Jul. 18, 2012 (8 pages).

International Search Report for International Application No. PCT/US2012/039850, dated Oct. 3, 2012 (3 pages).

Jeong et al., "Novel role of Pin1 induction in type II collagen-mediated rheumatoid arthritis," J Immunol. 183(10):6689-97 (2009).

Kim et al., "Controlled release of all-trans-retinoic acid from PEGylated gelatin nanopaticles by enzymatic degradation," Biotechnol. Bioprocess. Eng. 4(3):215-8 (1999).

Lam et al., "Prolyl isomerase Pin1 is highly expressed in Her2-positive breast cancer and regulates erbB2 protein stability," Mol Cancer 7(91):1-12 (2008).

Lu et al., "Prolyl isomerase Pin1 in cancer," Cell Res. 24(9):1033-49 (2014).

Lu et al., "The prolyl isomerase PIN1: a pivotal new twist in phosphorylation signalling and disease," Nat Rev Mol Cell Biol. 8(11):904-16 (2007).

Nakamura et al., "Proline isomer-specific antibodies reveal the early pathogenic tau conformation in Alzheimer's disease" Cell. 149(1):232-44 (2012).

Office Action for U.S. Appl. No. 14/334,052, dated Sep. 25, 2015 (29 pages).

Office Action for U.S. Appl. No. 14/334,052, dated Nov. 20, 2014 (21 pages).

Ramlau et al., "Randomized phase III trial comparing bexarotene (L1069-49)/cisplatin/vinorelbine with cisplatin/vinorelbine in chemotherapy-naive patients with advanced or metastatic non-small-cell lung cancer: SPIRIT I," J Clin Oncol. 26(11):1886-92 (2008).

Wei et al., "Active Pin1 is a key target of all-trans retinoic acid in acute promyelocytic leukemia and breast cancer," Nat Med. 21(5):457-66 (2015).

Written Opinion of the International Searching Authority for International Application No. PCT/US2012/039850, dated Oct. 3, 2012 (5 pages).

Wulf et al., "Pin1 is overexpressed in breast cancer and cooperates with Ras signaling in increasing the transcriptional activity of c-Jun towards cyclin D1," EMBO J. 20(13):3459-72 (2001).

Zhou et al., "The isomerase PIN1 controls numerous cancer-driving pathways and is a unique drug target," Nat Rev Cancer. 16(7):463-78 (2016) (16 pages).

FIG. 3A
| Pin1 missense mutation | Cancer type |
|---|---|
| Q33K | Skin melanoma |
| E100D | Colon and rectum adenocarcinoma |
| E145K | Head and neck SCC |
| G148R | Stomach adenocarcinoma |
| P149S | Skin melanoma |
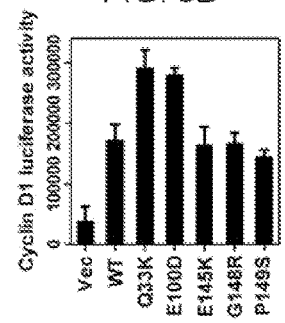
FIG. 3B
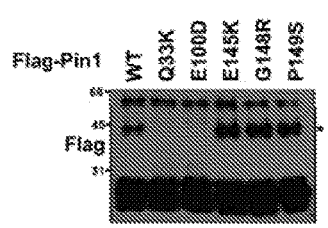
FIG. 3C
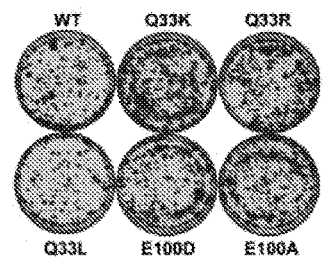
FIG. 3D
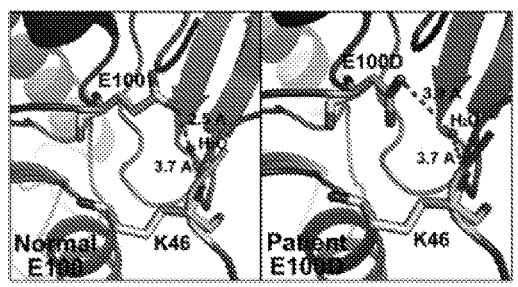
FIG. 3E
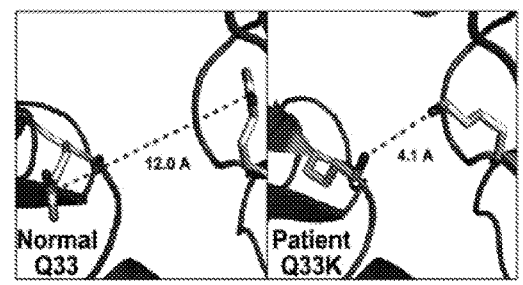
FIG. 3F 13-cis-retinoic acid (13cRA)

All trans retinoic acid (ATRA)

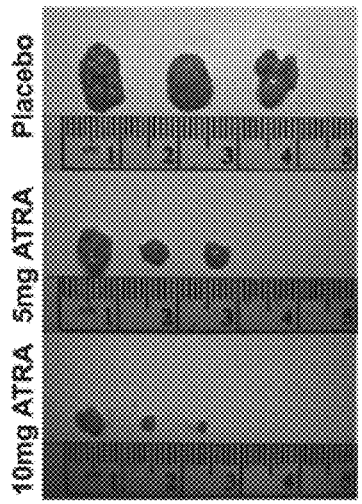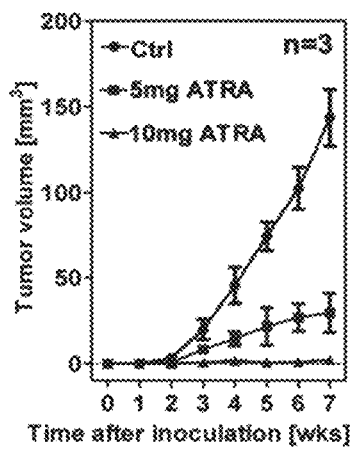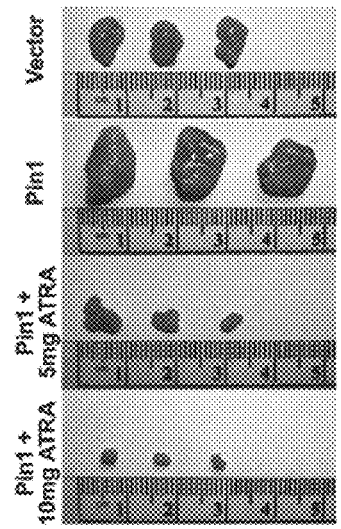
FIG. 7A  FIG. 7B  FIG. 7C
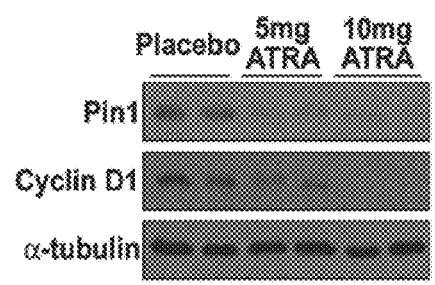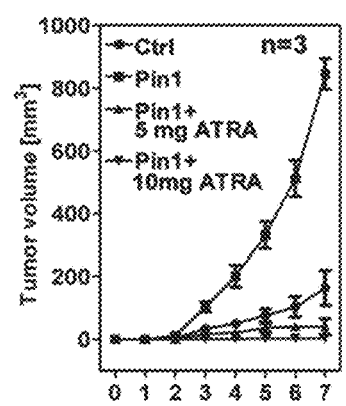
FIG. 7D  FIG. 7E
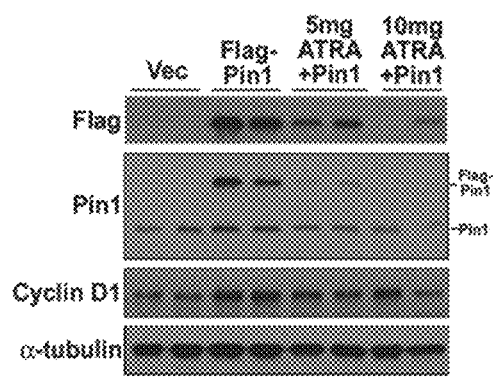
FIG. 7F FIG. 7G
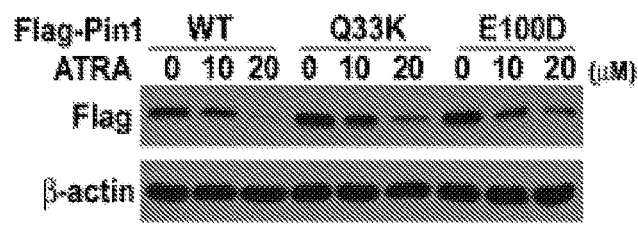
FIG. 7H
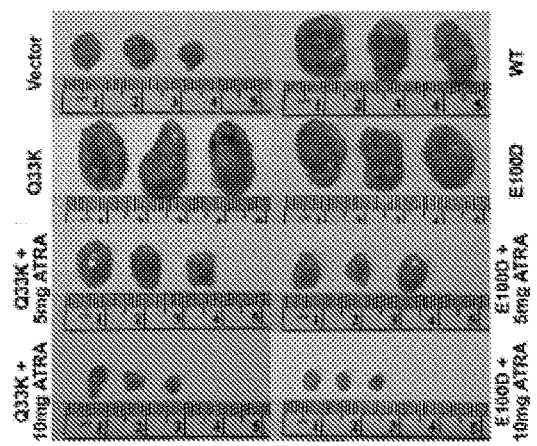
FIG. 7I
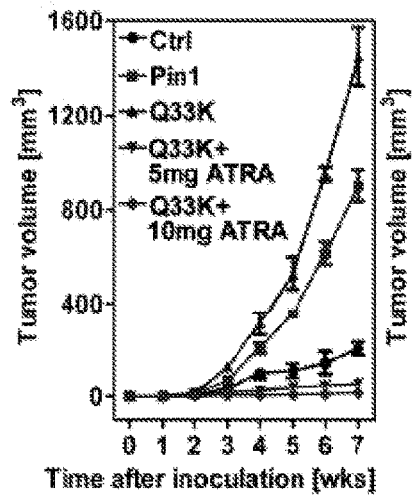
FIG. 7K
FIG. 7J
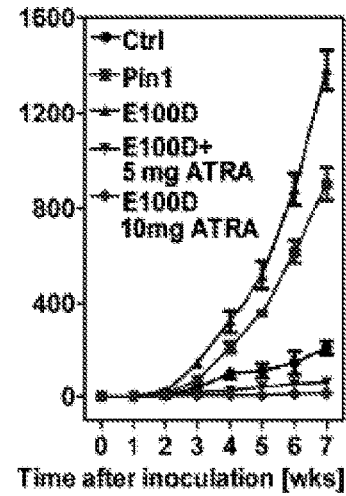

ATRA FOR MODULATING PIN1 ACTIVITY AND STABILITY

STATEMENT AS TO FEDERALLY FUNDED RESEARCH

This invention was made with government support under Grant No. DA031663, CA167677, CA122434, AG039405 and HL111430 awarded by the National Institutes of Health. The government has certain rights in the invention.

BACKGROUND

Field of the Disclosure

The present disclosure relates in general to compositions and methods for inhibiting Pin1 and, more specifically, to all-trans-retinoic acid (ATRA) for modulating Pin1 activity and stability.

Background Information

Cancers represent a leading health problem. The treatment varies based on the type of cancer and stage. The stage of a cancer refers to how much it has grown and whether the tumor has spread from its original location or metastasized. One of the more recent strategies has been with targeted anti-cancer therapy based on compounds that interfere with specific cellular targets directly connected with pathogenic events. Such therapies are expected to selectively target tumor cells, thus allowing for strong anti-cancer effects, while minimizing toxicities and side-effects. A number of such target-based anti-cancer therapies are now successfully used in routine clinical practice. For example, in chronic myelogenous leukemia (CML), the Abelson tyrosine kinase inhibitor Imatinib (Gleevec) targets the activity of BCR-ABL oncoprotein, thus leading to significant remission of the disease in patients.

All-trans-retinoic acid (ATRA) has long been known for its effects on embryonic development, cellular growth, and differentiation. ATRA and associated retinoids are lipophilic molecules that can pass through plasma membranes, and enter the nucleus where they bind Retinoic Acid Receptors (RARs). These receptors are members of the nuclear receptor family, and can be divided into 2 subgroups, RAR and Retinoid X Receptor (RXR). ATRA can bind both but has higher affinity to RAR. Binding of ATRA to RAR or RXR induces allosteric changes that allow the receptors to bind specific DNA recognition sites, and regulate gene transcription. ATRA is currently used in the treatment of several types of cancers, including Acute Promyelocytic Leukemia (APL), squamous cell carcinoma of the head and neck, and skin cancer, among others, for its actions on cellular proliferation, and differentiation.

Pin1 is a highly conserved protein that catalyzes the isomerization of only phosphorylated Ser/Thr-Pro bonds. In addition, Pin1 includes an N-terminal WW domain, which functions as a phosphorylated Ser/Thr-Pro binding module. The specificity of Pin1 activity is pivotal for cancer cell growth; depletion or mutations of Pin1 cause growth arrest, affect cell cycle checkpoints, and induce premature mitotic entry, mitotic arrest, and apoptosis in human tumor cells. Furthermore, research supports a pivotal role for Pin1 in tumorigenesis by activating many cancer-driving pathways. Pin1 overexpression is prevalent in approximately 60 different human cancer types examined, and the level of Pin1 overexpression is tightly linked to poor clinical outcome of cancer patients. In contrast, the people who carry some genetic variants that reduce Pin1 expression have lower risk for different cancers.

A common and central signaling mechanism in tumorigenesis is Proline-directed phosphorylation, which has been shown to be further regulated by Pin1-catalyzed cis-trans isomerization. In addition, Pin1 has been shown to promote tumorigenesis and tumor aggressiveness by activating a plurality of oncogenes, and inhibiting a plurality of tumor suppressors in a Proline-directed phosphorylation dependent manner.

Although cancer drugs that target specific molecular targets, proteins, and pathways have improved the treatment of cancers, they are often less effective, subject to resistance, or lose efficacy in the long term due to activation of many alternative pro-tumorigenic pathways. It has become evident that in aggressive or drug-resistant cancers, a number of genetic or non-genetic changes activate oncogenes/growth enhancers and/or inactivate tumor suppressors/growth inhibitors to turn on a wide range of interactive and/or redundant pathways. Therefore, a significant challenge remains to address how to maintain inhibition of multiple oncogenic pathways that concurrently block multiple oncogenic pathways.

For the foregoing reasons, there is a need for identifying Pin1 inhibitors selectively for cancer cells to create drugs that pharmacologically ablate the activated form of Pin1 to block multiple oncogenic pathways simultaneously.

SUMMARY OF THE INVENTION

The present disclosure describes and identifies genetic and biochemical mechanisms of Pin1 activation in cancer. In one aspect of the present disclosure, innovative high-throughput screening (HTS) for compounds selectively against activated Pin1 was developed, which led to the discovery of all-trans-retinoic acid (ATRA) as a new Pin1 inhibitor for treating diseases associated with aberrant levels of activated Pin1 or overexpression of Pin1. High-throughput screening against active Pin1 identifies that ATRA binds and ablates the active Pin1 monomer, but not the inactive Pin1 dimer.

The present disclosure describes methods of treating diseases characterized by elevated Pin1 marker levels or the presence of Pin1 driver mutations in a subject by administering ATRA or ATRA-containing formulations. ATRA is currently approved for treating acute promyelocytic leukemia (APL) although the mechanism by which ATRA ablates the leukemia cells remains elusive because the ability of ATRA to activate RARs is not sufficient to ablate the leukemia cells. Additionally, the disclosure features methods of treating diseases characterized by elevated Pin1-related biomarkers, levels of protein expression, levels of Pin1 activation through protein modifications, and/or presence of driver mutations in a subject by administering ATRA or ATRA-containing formulations in combination with anti-cancer, anti-inflammatory, anti-viral, or anti-microbial compounds, among others.

In one embodiment, the present disclosure describes Pin1 activation mechanisms and therapeutic potential in overexpressed Pin1-associated diseases and conditions, such as cancer, lupus, asthma, and cocaine addiction, among others.

In one embodiment, the present disclosure describes ATRA or ATRA-containing formulation for modulating Pin1 activity and stability. Due to the efficient first pass metabolism of ATRA in humans and mammals resulting in a short half-life of ATRA of approximately 45 minutes, formulations that extend the presence of ATRA in the body or delay the metabolism of ATRA are useful for treatment of solid tumors and other diseases or conditions involving modification of Pin1 activity.

One aspect of the present disclosure is ATRA may have anti-cancer activity inducing PML-RARa degradation, as well as inhibiting multiple cancer-driving pathways at the same time via modifying Pin1 activity and protein stability. Additionally, ATRA may provide a rationale for developing additional potent and specific chemicals that are Pin1 inhibitors based on the co-crystal structure of ATRA and Pin1, which may be employed in cancer treatments including aggressive and drug-resistant cancers by simultaneously blocking numerous cancer-driving pathways, with relatively low toxicity.

Another aspect of the present disclosure is human cancer-derived Pin1 mutations, Q33K or E100D, which may keep Pin1 in the constitutively active monomer, and enhance Pin1 tumorigenic activity by disrupting Pin1 WW domain-mediated dimerization. Q33K and E100D may be driver mutations by promoting the active, monomeric form of Pin1 as supported by the Pin1 crystal structure, and molecular modeling. Additionally, post-translational protein modifications of Pin1 that can serve as biomarkers for identifying cancers or conditions that may benefit from treatment with ATRA, ATRA-containing formulations, or Pin1 inhibitors include deacetylation of K13 and K46 that promotes Pin1 active monomer and function, dephosphorylation of S71 that activates Pin1 catalytic activity and function, dephosphorylation of S16 that increases Pin1 substrate binding (PMID: 11723108), desumoylation of K6 and K63 that promotes Pin1 oncogenic activity, or phosphorylation of S65 that increases Pin1 protein stability (PMID: 16118204), and phosphorylation of S138 that increases Pin1 catalytic activity and nuclear translocation (PMID: 22566623).

In one embodiment, ATRA or ATRA-containing formulations may bind and inhibit enzymatic activity of the activated Pin1 monomer, and also induce degradation of the activated Pin1 monomer. ATRA or ATRA-containing formulations have no effect on the inactivate Pin1 dimer in normal cells.

Yet another aspect of the present disclosure is the identification of the binding mechanism of ATRA with Pin1, where the binding mechanism may confirm ATRA binding specificity and also explain why ATRA has significantly less potency against Pin1 in normal cells because Ser71 is normally phosphorylated, which prevents ATRA binding. Retinoids with a —COOH group may inhibit Pin1, but those with —CHOH or —CHO or —COOCH$_3$ groups may be inactive. In this disclosure, it is shown that on the co-crystal structure of Pin1 and ATRA, the carboxylic acid of ATRA forms H-bonds with R68 and K63 in the substrate phosphate-binding pocket of Pin1, while the cyclohexane group of ATRA on the other end forms hydrophobic interactions with critical residues in the Pin1 Pro-binding pocket.

Another embodiment of the present disclosure describes the synergy of combining ATRA to improve inhibition of the activated Pin1 monomer by using DAPK1 inhibition to open the ATRA-binding pocket or SIRT1 inhibition to promote acetylated Pin1 K13 and K46 and therefore further reducing the Pin1 monomer reservoir.

In an embodiment, ATRA may ablate Pin1 to promote PML-RARα degradation. Active Pin1 may act on phosphorylated PML-RARa to increase its protein stability. Pin1-ATRA complex may potently induce Pin1 degradation, which highly correlates with PML-RARa degradation in the bone marrow.

In further embodiments, Pin1-ATRA complex may potently inhibit aggressive cancer by ablating Pin1 and therefore suppress multiple cancer-driving molecules at the same time in cell and mouse models. Specifically, ATRA treatment induced the degradation and ablation of Pin1 and turned off many Pin1-dependent oncogenes while turning on Pin1-dependent tumor suppressors in cancer cell lines. These results mirrored experiments using Pin1 knock-down in the same cancer cell lines. Both ATRA and Pin1 knockdown had the same effect on oncogene and tumor suppressor expression.

In various embodiments, understanding Pin1-ATRA complex binding mechanisms may be employed to develop commercial products, such as any suitable ATRA and any long-lasting ATRA-containing formulations to treat cancers and other Pin1-related diseases such as lupus and asthma using Pin1 markers; any suitable new generation of ATRA-related more potent, more specific, and/or longer half-life Pin1 inhibitors that may bind to Pin1 active site based on the Pin1-ATRA structure to treat cancers and other Pin1-related diseases such as lupus and asthma using Pin1 markers; any suitable ATRA-containing formulation, and ATRA-related more potent, more specific, and/or longer half-life Pin1 inhibitors in combination with other existing therapies including chemotherapy or molecularly targeted drugs and other standard of care; and Pin1 markers that may suggest an elevated monomeric activated Pin1, which may include Pin1 Q33K or E100D driver mutation, Pin1 overexpression, dephosphorylation on Ser71, dephosphorylation of S16, phosphorylation of S65, phosphorylation of S138, deacetylation on Lys13 and Lys46, and/or desumolation on Lys6, and Lys63, among others.

In a first aspect, the invention features a pharmaceutical composition including an effective amount of a retinoid, in which the composition is formulated for long-term delivery of the retinoid after delivery of the composition to a subject. In certain embodiments, the delivery is by injection into the subject.

In some embodiments, the composition is formulated as an injectable depot system, an injectable drug suspension, an injectable microsphere, or an injectable gel.

In certain embodiments, the injectable drug suspension is an oil-based suspension.

In various embodiments, the composition is formulated for intravenous injection or intramuscular injection. In particular embodiments, the composition is formulated as an injectable gel and for intramuscular injection. In specific embodiments, the injectable gel remains in the muscle for at least 4-6 weeks after injection.

In some embodiments, the composition is formulated to delay the metabolism of the retinoid. In certain embodiments, the composition includes one or more liposomes including the retinoid.

In various embodiments, the composition further includes a pharmaceutically acceptable excipient.

In some embodiments, the retinoid is all-trans retinoic acid (ATRA).

In further embodiments, the invention features a method of treating or preventing a Pin1-related disorder in a subject in need thereof. The method involves administering the composition of any of the above aspects to the subject.

In certain embodiments, the Pin1-related disorder is a cancer, an immune disorder, or cocaine addiction.

In particular embodiments, the cancer is selected from the group consisting of: acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia, Hodgkin's disease, non-Hodgkin's disease, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, esophageal cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma.

In a specific embodiment, the cancer is breast cancer.

In particular embodiments, the immune disorder is asthma or lupus.

In some embodiments, the subject is determined to have elevated levels of a Pin1 marker prior to the administration.

In various embodiments, the method further includes administering a second therapeutic compound.

In certain embodiments, the second therapeutic compound is a chemotherapeutic compound, a DAPK inhibitor, a SIRT1 inhibitor, a deacetylase inhibitor, a second Pin1 inhibitor, a Plk1 inhibitor, an anti-inflammatory compound, an antimicrobial compound, an antiviral compound, or any combination thereof. In particular embodiments, the SIRT1 inhibitor is NAM or Splito. In other embodiments, the deactylase inhibitor is garcinol or anacardic acid. In further embodiments, the second Pin1 inhibitor is PiB, EGCG, juglone or a second retinoid. In a specific embodiment, the second retinoid is 13-cis-retinoic acid. In alternate embodiments, the Plk1 inhibitor is selected from the group consisting of: BI-2536, volasertib, wortmannin, GSK461364A, rigosertib, cyclapolin 9, cyclapolin 1, GW 843682X, SBE 13 hydrochloride, MLN0905, R03280, HMN-214, HMN-176, NMS-P937, an siRNA, or a dominant-negative form of Plk1.

In certain embodiments, the composition and the second therapeutic compound are administered separately or in a single formulation.

Numerous other aspects, features and benefits of the present disclosure may be made apparent from the following detailed description taken together with the drawing figures.

BRIEF DESCRIPTION OF THE DRAWINGS

The present disclosure can be better understood by referring to the following figures. The components in the figures are not necessarily to scale, emphasis instead being placed upon illustrating the principles of the disclosure. In the figures, reference numerals designate corresponding parts throughout the different views.

Figures 1A, 1B:
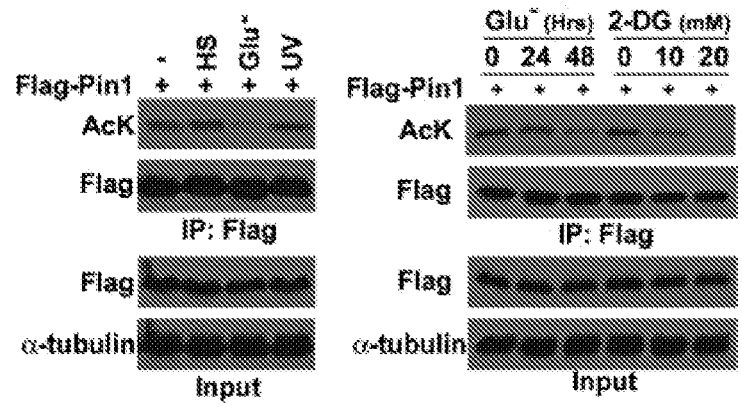
FIG. 1 shows that SIRT1 activation increases Pin1 deacetylation.

(A) Glucose starvation induced Pin1 deacetylation in cells. Cells were transfected with Flag-Pin1 and subjected to various stresses, followed by Flag IP before with immunoblotting acetyl-lysine (AcK) or Flag antibody. Glu-, glucose starvation; HS, heat shock; UV, UV radiation.

(B) 2-deoxyglucose (2-DG) along with Glu-dose-dependently increased Pin1 deacetylation.

(C) Overexpression of p300-HA increased Pin1 acetylation in cells. Various histone acetyl transferases were co-transfected with Flag-Pin1 into cells, followed by assaying acetylated Pin1.

(D) p300 inhibitors, Garcinol (Gar) and Anacardic acid (AnAc), reversed p300-increased Pin1 acetylation.

FIG. 2 illustrates that deacetylation at K13 and K46 favors Pin1 monomer and increases Pin1 activity.

(A) WT SIRT1, but not its inactive H363Y mutant disrupted Pin1 dimerization, as shown by Co-IP of GFP-Pin1 and HA-Pin1.

(B) Structural basis of Pin1 acetylation favoring dimers. Molecular modeling analysis revealed that although there are two water-mediated hydrogen bonds between K46 back bone and E100 in native Pin1 (left panel), K46 acetylation formed additional hydrogen bonds between the K46 side chain with the backbone and side chain of E101 and D102 (right panel).

FIG. 3 shows that cancer-derived Q33K and E100D Pin1 mutations behave monomeric and tumorigenic.

(A) Summary of human Pin1 missense mutations from the cBio Cancer Genomics Portal and the COSMIC database.

(B) Q33K and E100D mutations increased Pin1 activity, as assayed by activating the cyclin D1 promoter (B).

(C) Q33K and E100D mutations increasing Pin1 oncogenic activity, as assayed by enhancing cell growth.

(D) Q33K and E100D mutations increasing Pin1 oncogenic activity, as assayed by enhancing foci formation.

(E) The E100D mutation favors Pin1 monomer because the hydrogen bonds between E100D and K46 have longer distances than that between E100 and K46 in the WT dimer. Asterisk, Pin1 dimer (F) The Q33K mutation favors Pin1 monomer because the distance between two Q33K is much shorter than that between two Q33 in the WT dimer so that they repel each other.

FIG. 4 depicts the identification of ATRA as an inhibitor against Pin1 monomer.

(A) Summary plot of FP-HTS for Pin1 inhibitors, with 13-cis-retinoic acid having the lowest Z score, as determined by folds of standard deviation below the mean of each screening plate.

(B, C) Structures of cis (13cRA) and trans (ATRA) of retinoic acid.

(D, E) ATRA had much greater Pin1 binding than 13cRA after a 0.5 h incubation (D), but they had the same potent Pin1 binding after a 24 h incubation, which allows 13cRA to convert to ATRA (E).

(F) ATRA was the most potent Pin1 binder among retinoids tested and its carboxylic acid group was required for Pin1 binding.

FIG. 5 shows that genetic or pharmacological Pin1 ablation attenuates APL outcomes via inducing PML-RARa degradation.

(A, B) Pin1 KD reduced PML-RARa protein expression (A) and proliferation (B) of human APL NB4 cells, which was rescued by re-constitution of WT Pin1, but not its dead W34/63A mutant.

(C, D) Pin1 KD greatly reduced protein half-life of PML-RARa in NB4 cells (C, upper panel), which was rescued by re-constitution of WT Pin1, but not its dead W34/63A mutant (C, lower panel), with quantification data being presented in (D) (n=3).

(E) Doxycycline-inducible Pin1 KD greatly reduced PML-RARa protein levels in the bone marrow of human APL cell transplanted mice. Immunodeficient NSG mice were transplanted with 5×105 NB4 cells stably carrying inducible Tet-on shPin1 construct and received doxycycline food to induce Pin1 KD, followed by examining PML-RARa and Pin1 in the bone marrow.

(F, G) Doxycycline-inducible Pin1 KD reduced spleen size by 3 folds in human APL cell transplanted mice (F), with quantification data being presented in (G) (n=4).

(H) Doxycycline-inducible Pin1 KD increased disease-free survival of human APL cell transplanted mice.

(I) ATRA dose-dependently induced degradation of Pin1 and PML-RARa in human NB4 cells.

(J) Other structurally distinct Pin1 inhibitors, PiB, EGCG or Juglone also induced degradation of PML-RARa in a dose-dependent manner, although without inducing dramatic Pin1 degradation.

(K) Potentiated effects of ATRA with SIRT1 inhibitors, NAM or Splito, on cell growth of NB4.

(L-N) Three distinct Pin1 inhibitors induced degradation of PML-RARa and reduced spleen size in situ APL mouse model. Sublethally irradiated C57BL/6J mice were transplanted with 1×106 APL cells isolated from the hCG-PML-RARa transgenic mice and, 5 days after, treated with ATRA, EGCG, Juglone or placebo for 3 weeks, followed by examining PML-RARa and Pin1 expression in the bone marrow (L) and the size of spleen in mice (M), with quantification being shown in (N) (n=10).

(O-Q) ATRA reduced Pin1 and PML-RARa in the bone marrow in APL patients in a time dependent manner. Bone marrow samples from APL patients before or after 3 or 10 days of ATRA treatment were immunostained with anti-Pin1 and anti-PML antibodies. Both Pin1 and PML-RARα were significantly reduced only 3 days after ATRA treatment and become even more dramatic 10 days after ATRA treatment (0). Note, PML-RARα/PML was still diffusely distributed to the entire nucleus in APL cells that contained more Pin1 (Red arrows), but almost exclusively localized to the PML body (likely reflecting endogenous PML) in APL cells that contained much less Pin1 (yellow arrows). Relative levels of Pin1 (P) in the nucleus and PML-RARα in the nuclear plasma outside of the PML nuclear body (Q) were semi-quantified (n=3).

FIG. 6 shows that ATRA ablates monomeric activated Pin1 to inhibit many cancer-driving pathways at the same time in human breast cancer cells.

(A, B) ATRA dose-dependently inhibited the ability of Pin1 over-expression to induce centrosome amplification in NIH3T3 cells (A), with cells containing over 2 centrosomes being quantified from 3 independent experiments with over 100 cells in each (B).

(C) ATRA dose-dependently inhibited the ability of Pin1 to activate the cyclin D1 promoter.

(D, E) ATRA dose-dependently inhibited the ability of Pin1 to enhance foci formation of MDA-MB-231 cells (D), with quantification results being presented (E) (n=3).

(F, G) Anti-proliferative effects of ATRA (F) and their correlation with Pin1 S71 phosphorylation (G) in various human normal and breast cancer cell lines.

(H) S71 phosphorylation formed hydrogen bonds with Arg69 and Lys63 of the PPIase pocket, preventing ATRA from binding to the same pocket in Pin1.

(I, J) Either ATRA (I) or inducible Pin1 KD (J) shared the same ability to reduce protein levels of Pin1 and its substrate oncogenes including cyclin D1, HER2, ERα, Akt, NFkB/p65, c-Jun and PKM2 as well as to increase protein levels of Pin1 substrate tumor suppressors, Smad and SMRT, in breast cancer MDA-MB-231, SKBR3 and T47D cells, with ATRA having little effects on normal MCF10A cells. TNBC, triple negative breast cancer.

FIG. 7 shows that slow-releasing of ATRA inhibits human triple negative breast cancer tumor growth in mice even after overexpression of Pin1 or its cancer-driving mutants.

(A, B) ATRA inhibited tumor growth of MDA-MB-231 cells in mice. Female nude mice were flank-inoculated with $2\times10^6$ MDA-MB-231 cells and, 1 week later, implanted with 5 or 10 mg 21 day slow-releasing ATRA pellets. Tumor sizes were measured weekly and tumor tissues were collected from the mice after 7 weeks (A). Curves of tumor volume were plotted after calculation with formula of $L \times W^2 \times 0.52$ (B) (n=3).

(C) ATRA dose-dependently induced degradations of Pin1 and its downstream target cyclin D1 in xenograft breast tumors.

(D, E) ATRA inhibited tumor growth of MDA-MB-231 cells in mice, even after Pin1 over-expression. MDA-MB-231 cells stably expressing Flag-Pin1 or control vector were inoculated into female nude mice followed by ATRA treatment. Tumors were collected 7 weeks post-treatment (D). Quantitative curves of tumor volume were plotted after calculation (E) (n=3).

(F) ATRA dose-dependently induced degradations of both endogenous and exogenous Pin1 as well as cyclin D1 in xenograft breast tumors.

(G) ATRA dose-dependently induced degradations of WT-Pin1 or its monomeric Q33K or E100D mutant in MDA-MB-231 cells.

(H-J) ATRA inhibited tumor growth of MDA-MB-231 cells in mice, even after over-expression of monomeric Q33K or E100D Pin1 mutant. Nude mice were injected with 2×106 MDA-MB-231 cells and treated with ATRA pellets at indicated dosages. Tumors were harvested 7 weeks later. Quantitative curve of tumor volumes developed by Q33K (I) or E100D (J)-expressing MDA-MB-231 in the nude mice (n=3).

(K) ATRA dose-dependently induced degradations of Pin1 Q33K or E100D mutant in xenograft breast tumors.

FIG. 8 shows that Pin1 KO reduced Th2 response and asthma after OVA allergen challenge in mice.

(A) Pin1 KO reduced OVA-induced asthma.
(B) Pin1 KO reduced OVA-induced Th2 response.
(C) Pin1 KO reduced total cells in BAL.
(D) Pin1 KO reduced eosinophils in BAL.

FIG. 9 shows that Pin1 KO potently inhibited expression of autoimmunity of B6.MRL/lpr lupus prone mice.

(A) Pin1 knockout potently reduced fur loss, skin papillomas and acanthosis, and lymphoid hyperplasia in B6.MRL/lpr lupus prone mice.

(B) Size of the spleen and lymph node.
(C) Skin hyperkeratosis.
(D) Deposition of IgG, complement C3 and CD68 in the glomerulus.
(E) Production of anti-double strand DNA antibodies and IL-2 and IL-17 cytokines.
(F) Proteinuria and CD4 and CD8 double-negative T cell population in B6.MRL/lpr lupus prone mice.

FIG. 10 illustrates ATRA inhibited expression of autoimmunity of MRL/lpr lupus prone mice. ATRA potently reduced (A) ATRA potently reduced fur loss, skin papillomas and acanthosis, and lymphoid hyperplasia.
(B) ATRA reduced the size of the spleen and lymph node.
(C) ATRA reduced skin hyperkeratosis.

(D) ATRA reduced the deposition of IgG, complement C3 and CD68 into the glomerulus in MRL/lpr lupus prone mice.

DETAILED DESCRIPTION

The present disclosure is here described in detail with reference to embodiments illustrated in the drawings, which form a part here. Other embodiments may be used and/or other changes may be made without departing from the spirit or scope of the present disclosure. The illustrative embodiments described in the detailed description are not meant to be limiting of the subject matter presented here.

Definitions

As used here, the following terms may have the following definitions:

"ATRA" refers to all-trans-retinoic acid, which is the carboxylic acid form of Vitamin A.

"ATRA-containing formulation" refers to any long-lasting ATRA formulations that increase the half-life or impeded the metabolism of ATRA in the body.

"Half-life" refers to the duration of action of a drug and the period of time required for the concentration or amount of drug in the body to be reduced by one-half.

"Pin1" refers to a peptidyl-prolyl cis/trans isomerase, NIMA-interacting 1 that isomerizes only phosphorylated Serine/Threonine-Proline motifs.

"Dimer" refers to a chemical entity including two structurally similar monomers joined by bonds that can be strong or weak, covalent or intermolecular.

"Binding pocket" refers to a region of a molecule or molecular complex that favorably associates with another chemical compound as a result of its shape and charge.

"Substrate" refers to a molecule upon which an enzyme acts.

"Activity" refers to a measurable amount of a specific function or role performed by a biological entity in a Biophysical Process, Biochemical Reaction, or Biochemical Process.

"Stability" refers to the ability of a protein to maintain its native conformation and function in response to changes in environmental factors, such as temperature, pH, and ionic strength.

"Potency" refers to a measure of the activity of a drug in a biological system.

"Sustained release dosage form" refers to the type of dosage form in which a portion (i.e., initial dose) of the drug may be released immediately, in order to achieve desired therapeutic response more promptly, and the remaining (maintenance dose) may then be released slowly there by achieving a therapeutic level which is prolonged, but not maintained constant. Sustained release implies slow release of the drug over a time period. It may or may not be controlled release.

"Treatment" refers to the application or administration of a therapeutic agent (e.g., any suitable ATRA, or any long-lasting ATRA formulations, or any suitable new generation of ATRA-related more potent, more specific, and/or longer half-life Pin1 inhibitors that may bind to Pin1 active site based on the Pin1-ATRA structure to a subject, or application or administration of a therapeutic agent to an isolated tissue or cell line from a subject, who has a disease, a symptom of disease or a predisposition toward a disease, with the purpose to cure, heal, alleviate, relieve, alter, remedy, ameliorate, improve or affect the disease, the symptoms of disease or the predisposition toward disease, or to slow the progression of the disease.

"Therapeutically effective amount" refers to a nontoxic but sufficient amount of an active pharmaceutical ingredient (API) to provide the desired therapeutic effect.

"Sample" and "Biological sample" refer to samples obtained from a mammal or a subject including Pin1 which can be used within the methods described herein, e.g., tissues, cells and biological fluids isolated from a subject, as well as tissues, cells and fluids present within a subject. Typical samples from a subject include tissue samples, tumor samples, blood, urine, biopsies, lymph, saliva, phlegm, and pus, among others.

DESCRIPTION OF THE INVENTION

The present disclosure features methods for treating diseases characterized by elevated Pin1 marker levels in a subject by administering ATRA or ATRA-containing formulations, a drug approved for treating acute promyelocytic leukemia (APL) with elusive mechanisms. Additionally, the disclosure features methods for treating diseases characterized by elevated Pin1 marker levels in a subject by administering ATRA or ATRA-containing formulations in combination with anti-cancer, anti-inflammatory, anti-viral, or anti-microbial compounds, among others.

In one aspect of the present embodiment, genetic and biochemical mechanisms of Pin1 activation in cancer are identified in order to develop innovative high throughput screening (HTS) for compounds selectively against activated Pin1, leading to the discovery of ATRA as a new Pin1 inhibitor for treating diseases associated to high levels of Pin1. High throughput screening against active Pin1 identifies that ATRA binds and ablates the activated Pin1 monomer.

The present disclosure demonstrates that Pin1 prolyl isomerase promotes tumorigenesis by activating numerous cancer-driving molecules, therefore providing an alternative approach by pharmacologically ablating the activated form of Pin1 selectively in cancer cells to block many oncogenic pathways at the same time.

In one embodiment, the present disclosure describes ATRA or ATRA-containing formulations for modulating Pin1 activity and stability.

In one embodiment, the present disclosure describes Pin1 activation mechanisms and therapeutic potential in overexpressed Pin1 associated diseases, such as cancer, lupus, asthma, and cocaine addiction, among others.

Pin1

Inhibitors of Pin1 are useful for treating immune disorders and proliferative disorders.

Pin1 is highly conserved and includes a protein-interacting module, called WW domain, and a catalytically active peptidyl-prolyl isomerase (PPIase). Pin1 is structurally and functionally distinct from members of two other well-characterized families of PPIases, the cyclophilins and the FKBPs. PPIases are ubiquitous enzymes that catalyze the relatively slow isomerization of proteins, allowing relaxation of local energetically unfavorable conformational states.

A common and central signaling mechanism in cell proliferation and transformation is Pro-directed Ser/Thr phosphorylation (pSer/Thr-Pro), which has been reported to be modulated by a large number of Pro-directed kinases and phosphatases. In fact, numerous oncogenes and tumor suppressors themselves are directly regulated by Pro-directed phosphorylation and/or can trigger signaling pathways involving Pro-directed phosphorylation. Because it has been demonstrated that the same kinases often phosphorylate both oncogenes and tumor suppressors, recent studies have been performed to understand how these phosphorylation events are coordinated to promote tumorigenesis.

Further research demonstrated that Pin1 Phosphorylation on serine/threonine-proline motifs restrains cis/trans prolyl isomerization, and also creates a binding site for the essential protein Pin1. Pin1 binds and regulates the activity of a defined subset of phosphoproteins, as well as participating in the timing of mitotic progression. Both structural and functional analyses have indicated that Pin1 includes a phosphoserine/threonine-binding module that binds phosphoproteins, and a catalytic activity that specifically isomerizes the phosphorylated phosphoserinelthreonine-proline. Both of these Pin1 activities are essential for Pin1 to carry out its function in vivo.

Phosphorylation on Ser/Thr residues immediately preceding Pro not only alters the prolyl isomerization rate, but also creates a binding site for the WW domain of Pin1. The WW domain acts as phosphoserine-binding module targeting Pin1 to a highly conserved subset of phosphoproteins. Furthermore, Pin1 displays a unique phosphorylation-dependent PPIase that specifically isomerizes phosphorylated Ser/Thr-Pro bonds and regulates the function of phosphoproteins.

Proline uniquely adopts cis and trans conformations, providing a backbone switch by prolyl cis-trans isomerization catalyzed by peptidyl-prolyl cis-trans isomerases (PPIases). A major advance in appreciating the importance of conformational changes after Pro-directed phosphorylation was the identification of the unique PPIase Pin1. Using its protein-targeting WW domain, Pin1 binds to specific pSer/Thr-Pro motif(s) that target Pin1 close to its substrates, where its PPIase domain catalyzes cis-trans isomerization of the pSer/Thr-Pro motifs, which cannot be effectively catalyzed by other known PPIases. Increasing evidence has supported a pivotal role for Pin1 in tumorigenesis.

Pin1 has been shown to be regulated by multiple mechanisms, including transcriptional activation by E2F, inhibiting phosphorylation by DAPK1, activating phosphorylation by PLK or MLK3, and/or activating desumoylation by SENP1. Pin1 overexpression is prevalent in approximately 60 different human cancer types and high Pin1 levels have been shown to correlate with poor clinical outcome in prostate, lung, esophageal, and breast cancers. In contrast, the Pin1 polymorphisms that reduce Pin1 expression are associated with lower risk for multiple cancers in humans, including breast cancer. Moreover, Pin1 knockout (−/−, KO) in mice are resistant to cancer development even induced by oncogenes, such as MMTV-Ras or -HER2. Conversely, Pin1 overexpression results in centrosome amplification, chromosome instability, and breast cancer development in vitro and in vivo.

Pin1 may activate a plurality of oncogenes/growth enhancers, such as c-Jun, b-catenin, cyclin D1, NF-kB/p65, Raf-1, c-fos, AIB1, Hbx, Stat3, HER2/Neu, Mcl-1, Notch, Akt, c-Rel, v-Rel, Tax, ERa, SF-1, mutant p53, PTP-PEST, PKM2, and c-Myc, among others. Pin1 may also inactivate a plurality of tumor suppressors/growth inhibitors, such as SMRT, PML, FOXOs, RARa, Smad, TRF1, Fbw7, Rb, AMPK, and RUNX3, among others. Thus, Pin1 may amplify oncogenic pathways in the positive and negative feedback mechanisms to turn on numerous oncogenes and/ or turn off many tumor suppressors at the same time. Small molecule inhibitors selectively against Pin1 in cancer cells might have a unique and desirable property to block numerous cancer-driving pathways at the same time.

Pin1 Activation Mechanisms in Cell Proliferation

It was identified that cancer-derived genetic mutations or SIRT1-mediated deacetylation keep Pin1 in a constitutively active monomer by disrupting WW domain-mediated dimerization. Using these mechanistic insights, innovative high throughput screening for compounds selectively against activated Pin1 was developed.

ATRA

All-trans retinoic acid (ATRA) is one of the active metabolites of Vitamin A. It has long been known for its effects on embryonic development, cellular growth, and differentiation. ATRA and associated retinoids are lipophilic molecules that can pass through plasma membranes and enter the nucleus where they bind retinoic acid receptors (RARs). These receptors are members of the nuclear receptor family and can be divided into 2 subgroups, Retinoid Acid Receptor (RAR) and Retinoid X Receptor (RXR). ATRA can bind both but has higher affinity to RAR. Ligation of ATRA to its receptors induces allosteric changes that allow RARs to bind specific DNA recognition sites and regulate gene transcription. Anti-inflammatory mechanisms by which ATRA down regulates T helper 1 (Th1) cytokines, such as IFN-γ, TNF-a and IL-12, appear to involve inhibition of both AP-1- and NF-KB-dependent transcription as well as destabilization of TNF-a mRNA. ATRA is currently used in the treatment of several types of cancers, including acute promyeiocytic leukemia (APL), squamous cell carcinoma of the head and neck, and skin cancer, for its actions on cellular proliferation and differentiation. Besides these latter, ATRA has the capacity to repair emphysematous lung damage by generating new septa and increasing alveolar surface area in adult lung. As such, it has been evaluated in the treatment of human emphysema.

ATRA selectively binds to and inhibits the activated Pin1 monomer and also induces its degradation. Only the trans form, ATRA, but not the cis form, 13cis Retinoic Acid (13cRA), of retinoic acid binds and inhibits Pin1. 13cRA needs to convert into ATRA to inhibit Pin1, being less potent than ATRA in vitro and in vivo. ATRA is the most potent compound against Pin1 among limited ATRA derivatives examined including Fenretinide and Bexarotene, and its carboxyl group is critical for inhibiting Pin1.

The specificity of ATRA towards activated Pin1 monomer may reveal that the carboxylic and aromatic moieties of ATRA interact with the Pin1 phosphate- and Pro-binding pockets in the Pin1 active site, respectively and that S71 phosphorylation may prevent ATRA from gaining access to the Pin1 active site by closing its binding pocket. Moreover, this specificity is further substantiated by the demonstration that the sensitivity of both breast cancer cells and APL cells to ATRA is enhanced by using DAPK1 inhibition to open the ATRA-binding pocket by preventing S71 phosphorylation or SIRT1 inhibition to reduce Pin1 monomer.

Therapeutical Indications for ATRA or ATRA-Containing Formulation

In one embodiment, the disclosure features a method of treating high levels of Pin1 associated diseases in a patient by determining Pin1 marker levels (e.g., reduced Ser71 phosphorylation) in a biological sample (e.g., tumor samples, blood, urine, biopsies, lymph, saliva, phlegm, and pus, among others) from the patient and administering a ATRA or an ATRA-containing formulation to the patient if the sample is determined to have elevated Pin1 marker levels.

In one embodiment, ATRA or ATRA-containing formulation may be used for treating a proliferative disorder in a subject by administering ATRA or ATRA-containing formulation to the subject in a therapeutically effective amount. The proliferative disorder can be any one or more selected from the group consisting of acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia, Hodgkin's disease, non-Hodgkin's disease, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma, among others.

In other embodiments, ATRA or ATRA-containing formulations may be used for treating other Pin1-related diseases and conditions, such as lupus, asthma, and cocaine addiction, among others.

In further embodiments, ATRA or ATRA-containing formulations or compositions may be employed for treating an immune disorder in a subject.

In one embodiment, ATRA or ATRA-containing formulation may be used in combination with other existing therapies including chemotherapy or molecularly targeted drugs and other standard of care.

In any of the foregoing aspects, the treatment can also include the administration of a second therapeutic compound. The second compound can be administered separately, or in a single formulation with ATRA. The second compound can be, e.g., an anti-cancer, anti-anti-inflammatory, anti-microbial, or anti-viral compound, among others. Additionally, or alternatively, any one of the foregoing methods can include determining Pin1 marker levels in the sample before, or before and after the administration of ATRA or ATRA-containing formulations.

In further embodiments, ATRA or ATRA-containing formulation may be combined with DAPK inhibitor or SIRT1 inhibitors, deacetylase inhibitors, among other Pin1 modifying enzyme inhibitors.

Furthermore, because Pin1 regulates multiple oncogenic pathways, Pin1 inhibition may behave synergistically with other anti-proliferative compounds.

In one embodiment, the second therapeutic compound can be selected from the group including corticosteroids, NSAIDs, COX-2 inhibitors, small molecule immunomodulators, non-steroidal immunophilin-dependent immunosuppressants, 5-amino salicylic acid, DMARDs, hydroxychloroquine sulfate, and penicillamine. Alternatively, the second therapeutic compound can be selected from the group including microtubule inhibitors, topoisomerase inhibitors, platins, alkylating agents, and anti-metabolites. The second therapeutic compound can also be selected from the group including 1-D-ribofuranosyl-1,2,4-triazole-3 carboxamide, 9→2-hydroxy-ethoxy methylguanine, adamantanamine, 5-iodo-2'-deoxyuridine, trifluorothymidine, interferon, adenine arabinoside, protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir, among others.

In yet another embodiment, the second therapeutic compound can be selected from the group including, Sorafenib, a microtubule inhibitor, a topoisomerase inhibitor, a platin, an alkylating agent, an anti-metabolite, paclitaxel, gemcitabine, doxorubicin, vinblastine, etoposide, 5-fluorouracil, carboplatin, altretamine, aminoglutethimide, amsacrine, anastrozole, azacitidine, bleomycin, busulfan, carmustine, chlorambucil, 2-chlorodeoxyadenosine, cisplatin, colchicine, cyclophosphamide, cytarabine, Cytoxan, dacarbazine, dactinomycin, daunorubicin, docetaxel, estramustine phosphate, floxuridine, fludarabine, gentuzumab, hexamethylmelamine, hydroxyurea, ifosfamide, imatinib, interferon, irinotecan, lomustine, mechlorethamine, melphalen, 6-mercaptopurine, methotrexate, mitomycin, mitotane, mitoxantrone, pentostatin, procarbazine, rituximab, streptozocin, tamoxifen, temozolomide, teniposide, 6-thioguanine, topotecan, trastuzumab, vincristine, vindesine, and/or vinorelbine, among others.

In one embodiment, pharmaceutical composition including ATRA may be formulated as a pill, ointment, cream, foam, capsule, or a liquid, among others, for administering to a subject.

In one embodiment, disclosed ATRA or ATRA-containing formulation may be included in a pharmaceutical composition, that may be a sustained release dosage form. Sustained release dosage form of ATRA-based composition may include sustained-release pharmaceutical compositions, such as injectable depot systems that may allow long-term delivery of ATRA.

In some embodiments, ATRA sustained release pharmaceutical formulations include intravenous (IV) injections, intramuscular (IM) injections, such as oil-based injections, injectable drug suspensions, injectable microspheres, and injectable gels, among other dosage forms.

In other embodiments, ATRA may be administrated as liposomal-based formulations of ATRA in a continuous time-releasing manner.

In one embodiment, ATRA may be included in gel dosage form, which may be injected directly into the muscle. The gel may disappear in about 4 to 6 weeks as it releases ATRA. The gel may be a thermally reversible gelling system that may be based on biodegradable triblock copolymer composed of PLGA-PEG-PLGA. Immediately upon injection and in response to body temperature, an insoluble gel depot may be formed.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

In other embodiments, any suitable new generation of ATRA-related more potent, more specific, and/or longer half-life Pin1 inhibitors that may go into Pin1 active sites based on the Pin1-ATRA structure may be employed to treat a plurality of cancers.

EXPERIMENTAL RESULTS

Effect of SIRT1 in Pin1 Deacetylation

FIG. 1 depicts HTS results for glucose starvation induced Pin1 deacetylation in cells 100. In order to perform glucose starvation induced Pin1 deacetylation in cells, cells were transfected with Flag-Pin1 and subjected to various stresses, followed by Flag IP before with immunoblotting acetyl-lysine (AcK) or Flag antibody. Glu-, glucose starvation; HS, heat shock; UV, UV radiation. 2-deoxyglucose (2-DG) along with Glu-dose-dependently increased Pin1 deacetylation. Overexpression of p300-HA increased Pin1 acetylation in cells. Various histone acetyl transferases were co-transfected with Flag-Pin1 into cells, followed by assaying acetylated Pin1. p300 inhibitors, Garcinol (Gar) and Anacardic acid (AnAc), reversed p300-increased Pin1 acetylation.

Figures 1C, 1D:
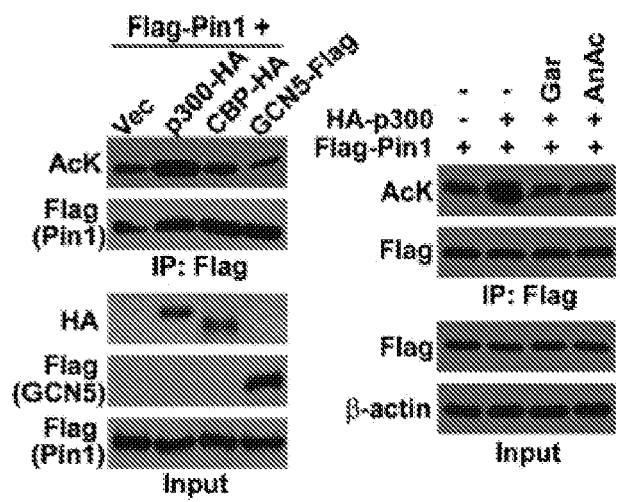

As shown in FIG. 1, among the stresses that tested included heat shock (HS), glucose starvation (Glu-) and UV, Glu-specifically reduced Pin1 acetylation without affecting its protein expression (FIG. 1A). To corroborate this notion, 2-deoxyglucose (2-DG), a glucose analog, was used to mimic glucose starvation (Wick et al., 1955). 2-DG treatment caused reduction in Pin1 acetylation in a time- or dose-dependent manner (FIG. 1B). Protein acetylation may be catalytically modulated by a particular pair of histone acetyl transferase (HAT) and deacetylase (HDAC) (Yang and Seto, 2007). To identify the HAT and HDAC that modulates Pin1 acetylation, Flag-tagged Pin1 was expressed with several HATs including p300, CBP or GCN5 in cells, followed by coimmunoprecipitation (Co-IP) with anti-Flag antibody and immunoblotting with anti-acetyl lysine antibody. Results in FIG. 1 show that Acetyl-Pin1 was significantly increased when p300 was over-expressed (FIG. 1C), which was reversed by two p300 inhibitors, Garcinol (Gar) and Anacardic acid (AnAc) (FIG. 10) (Bakana et al., 1987; Balasubramanyam et al., 2003). Results shown in FIG. 1 demonstrate that activation of SIRT1 increases Pin1 deacetylation.

Effect of Deacetylation at K13 and K46 Residues in Pin1 Activity

Figure 2A:
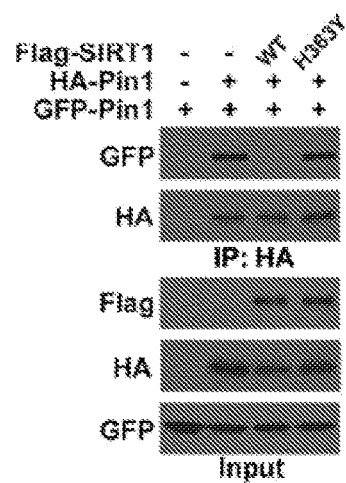

FIG. 2 shows the effect of deacetylation at K13 and K46 residues in Pin1 activity 200. To verify if the Pin1 dimer exists in vivo and is regulated by SIRT1-mediated deacetylation, performed Co-IP and crosslinking experiments were performed. FIG. 2 depicts HTS results for deacetylation at K13 and K46. In order to determine the effect of deacetylation a K13 and K46 residues, p300 acetylated Pin1 in the N-terminal WW domain in cells, cells were co-transfected with HA-p300 and Flag-Pin1 (WT), or its WW or PPI domain, followed by assaying acetylated Pin1. As shown in FIG. 2A, WT SIRT1, but not its inactive H363Y mutant, disrupted Pin1 dimerization.

To investigate the molecular impact of SIRT1-mediated deacetylation on Pin1, the spatial distribution of K13 and K46 in the Pin1 crystal structure was examined and it was found that Pin1 existed as a dimer. By analyzing Pin1 domains, it was concluded that acetylation occurred in the N-terminal WW domain which includes three lysine residues, K6, K13 and K46. Mutation of K13 or K46, but not K6, partially reduced Pin1 acetylation, while double mutation K13/46R completely abolished Pin1 acetylation, indicating that acetylation likely occurs of K13 and K46 (FIG. 2B), two highly evolutional conserved Lys residues.

Figure 2B:
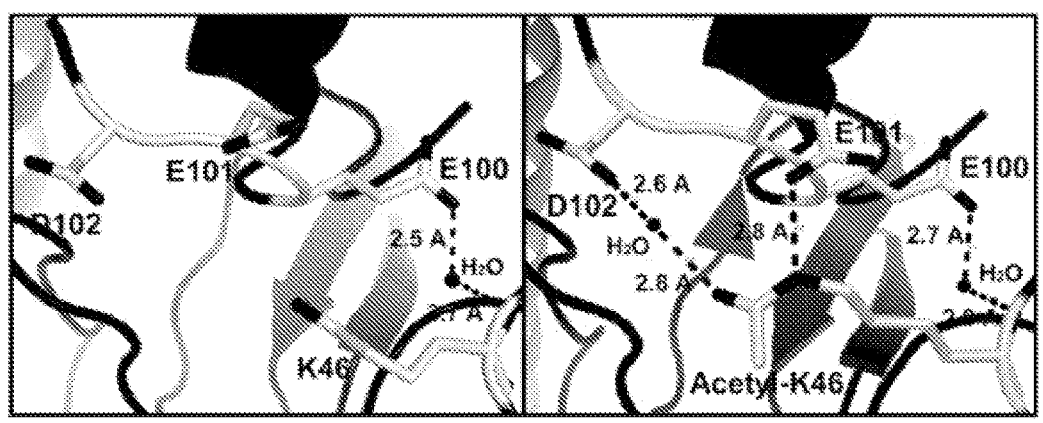

FIG. 2B illustrates molecular modeling providing the structural basis for Pin1 dimerization. As shown in FIG. 2B, left panel, in the native Pin1 dimer structure (Ranganathan et al., 1997), the backbone of K46 from one Pin1 monomer formed two water-mediated hydrogen bonds with the carboxylic side chain of E100 from the other Pin1 monomer. However, acetylation of K46 leads to the elongation of its side chain toward E101 and D102, to form additional hydrogen bonds, therefore favoring Pin1 dimerization shown in FIG. 2B, right panel. Both biochemical and structural results consistently support that Pin1 acetylation promotes dimer formation, while SIRT1-mediated deacetylation keeps Pin1 in a monomeric state. Results on FIG. 2 show that deacetylation at K13 and K46 promotes the formation of Pin1 Monomer, and therefore increases Pin1 activity.

Effect of Cancer-Derived Pin1 Mutations, Q33K and E100D in Pin1 Activity

To evaluate the clinical relevance of the Pin1 monomer in human cancers, Pin1 missense mutations were searched in the cBio Cancer Genomics Portal and the COSMIC database.

FIG. 3 depicts test results for Q33K and E100D in Pin1 activity 300. As shown in FIG. 3A, five Pin1 mutations in human cancers were identified and their oncogenic activity was examined. FIG. 3B illustrates how the Q33K and E100D mutations increased Pin1 oncogenic activity, as assayed by activating the cyclin D1 promoter, and enhancing cell growth and foci formation. Cells were expressed with various Pin1 mutants and were subjected to cyclin D1 promoter activity assay. As shown in FIG. 3B, the Q33K and E100D Pin1 mutants were notably more active than WT protein in activating the cyclin D1 promoter. FIG. 3C HTS results demonstrates that both Q33K and E100D kept Pin1 in a constitutively monomeric form. Moreover, Q33K or E100D mutations prevented Pin1 dimer formation (FIG. 3E).

FIG. 3D depicts the comparison of WT Pin1 with the 5 human mutations, Q33K, E100D, E145K, G148R, and P149 determining that cells stably expressing the Q33K or E100D mutant displayed increased proliferation, and formed more foci in colony forming assays.

Given that the Q33K or E100D mutation keeps Pin1 in the constitutively active monomer, their structural basis in the Pin1 dimer structure was examined. As shown in FIG. 3E, E100 localizes to the interface of the Pin1 dimer and binds to K46. However, the distance of one of the water-mediated hydrogen bonds between E100D and K46 (3.9 Å) was significantly longer than the WT one between E100 and K46 (2.5 Å), thus favoring Pin1 monomer and enhancing Pin1 tumorigenic activity.

The Q33K mutation was located in the center of the Pin1 dimer without interacting with any lysine residues of the interface. Molecular modeling analysis was carried out by imposing two energy-minimized monomeric Q33K forms on the dimer structure, shown in FIG. 3F. The closest residue to Q33K is another Q33K from the other half of the dimer. The distance between two positive charges of K33 was 4.1 Å, much shorter than that between two Q33 in WT Pin1, which is normally 12.0 Å. In such a short distance, two positive charges would repel each other and keep Pin1 in a monomeric state. Therefore, cancer-derived Q33K and E100D Pin1 mutations are monomeric and tumorigenic. Molecular modeling analysis demonstrates that E100D mutation favors Pin1 monomer likely because the hydrogen bonds between E100D and K46 have longer distances than that between E100 and K46 in the WT dimer, and that the Q33K mutation favors Pin1 monomer likely because the distance between two Q33K is much shorter than that between two Q33 in the WT dimer so that they repel each other.

Pin1 molecular modeling analysis in FIG. 3 shows that both cancer-derived Pin1 mutations, Q33K and E100D, promotes Pin1 in the monomeric state and enhance Pin1 tumorigenic activity.

ATRA Inhibition Effect on Activated Pin1 Monomer

Because Pin1 monomer is more oncogenic, the development of an inhibitor against the activated Pin1 monomer may be highly desirable due to their potential selectivity for cancer cells. In one aspect of the present disclosure, a robust HTS with a suitable probe is essential because no HTS has been available for identifying Pin1 inhibitors.

It has been previously shown that phosphorylation of Pin1 on S71 by the tumor suppressor DAPK1 inhibits Pin1 catalytic activity, and its oncogenic function by binding to the critical residues K63 and R69 in the catalytic active site, and that S71 phosphorylation prevents Pin1 from binding to pTide, a 4 residue non-natural peptide inhibitor (Bth-d-phos.Thr-Pip-Nal) that binds to Pin1 with high specificity and affinity (1.2 nM Kd), but cannot enter cells.

A FP-HTS screening for small molecule compounds that may compete with pTide for binding to dephosphorylated and thus activated Pin1 was developed. Pin1 PPIase domain was used instead of its full-length protein to ensure the identification of compounds that selectively target the catalytic site of monomeric Pin1. The HTS probe pTide was conjugated with FITC or TAMRA and assay conditions optimized to ensure that the probe only binds to the catalytic active site with certain essential residues, such as K63 and R69 (PDB: 2Q5A).

FIG. 4 shows study results 400 in which ATRA is identified as an inhibitor against Pin1 monomer. In this study, the phosphorylation-mimicking S71E mutant was unable to bind pTide. FP-HTS was carried out on a selected set of 8200 compound chemical libraries in the Harvard ICCB-L Screening Facility, of which 13-cis-retinoic acid (13cRA) was the No. 1 hit as a Pin1 inhibitor based on the lowest Z score as shown in FIG. 4A, which illustrates a summary plot of FP-HTS for Pin1 inhibitors, as determined by folds of standard deviation below the mean of each screening plate. As observed in FIGS. 4B and 4C, 13cRA and its pairing compound ATRA include a carboxylic acid and a hydrophobic six-membered aromatic ring.

Figure 4A:
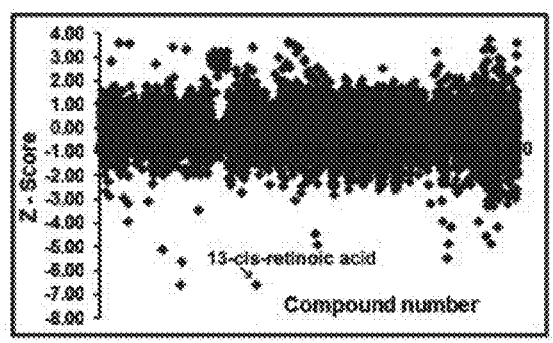
Figure 4B:
Figure 4C:
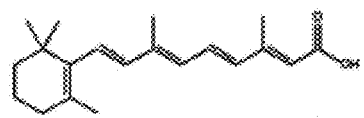
Figure 4D:
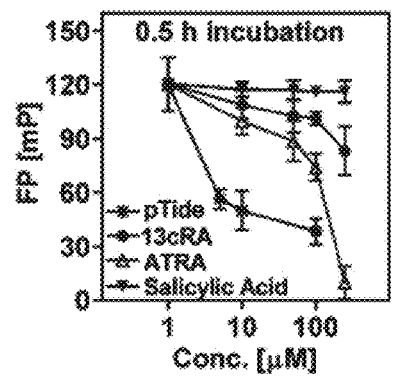
Figure 4E:
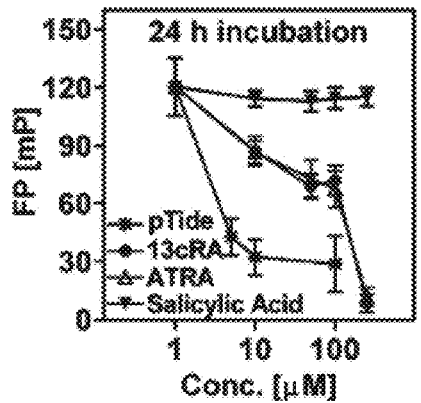

The ability of 13cRA and ATRA to bind Pin1 was verified in the short-term (0.5 h) or long-term (24 h) incubation with Pin1, followed by FP assay. Unlike the negative control salicylic acid, 13cRA and ATRA interacted with Pin1 in a dose-dependent manner. Moreover, ATRA was more potent than 13cRA after 0.5 h Pin1 incubation, but displayed the same potency after 24 h Pin1 incubation as shown in FIGS. 4D and 4E. These results suggest that Pin1 mainly binds to the trans form of retinoic acid (ATRA), and can bind to 13cRA after it is converted to trans, which does occur over time in vitro and in vivo. The ATRA-Pin1 interaction was confirmed using a TAMRA-conjugated probe to exclude autofluorescence artifacts. The dissociation constant, $K_d$, of ATRA to Pin1 was calculated to be 10.7±4.62 µM based on isothermal titration calorimetry assay. Drug specificity was examined using an in vitro PPIase assay with two other major PPIase families, cyclophilin, and FKBP12. Although ATRA inhibited neither cyclophilin nor FKBP12, 13cRA and ATRA completely inhibited Pin1 activity in a dose-dependent manner.

Figure 4F:
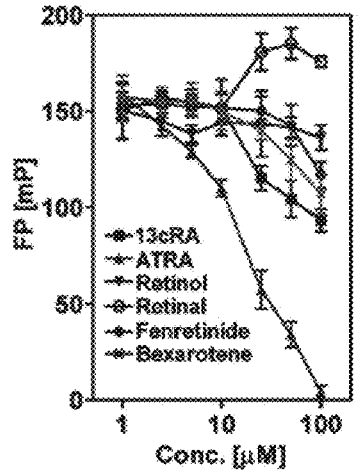

To examine whether the carboxylic acid in ATRA serves as an alternative of phosphate group that binds to Pin1, several structurally similar retinoids with substituted carboxylic or aromatic groups, as well as the new generation of retinoid drugs including Fenretinide and Bexarotene were tested for Pin1 binding. Out of retinoids tested, ATRA was the most potent against Pin1 as seen in FIG. 4F. Carboxylic acid group (—COOH)-substituted retinoids, including retinol (—OH), retinyl acetate (—OCOCH$_3$) and retinal (—CHO) were completely inactive, pointing to the importance of the carboxyl group as a pharmacophore for binding to Pin1 (FIG. 4F). Consistent with this idea, Fenretinide and Bexarotene showed only marginal Pin1 interaction (FIG. 4F), which might be attributed to the lack of a carboxylic group and/or additional modifications originally designed based on the RAR/RXR rationale.

Pin1 Inhibition by ATRA or Even Inducible KD Degrades PML-RARα and Treats APL in Cell and Mouse Models ATRA-induced PML-RARα degradation is associated with phosphorylation of the Ser581-Pro motif, which is the Pin1 binding site in RARα (S77 in RARa). Since Pin1 may increase many oncogene protein stabilities, Pin1 may bind to the pS581-Pro motif in PML-RARα and increase its protein stability.

To test this possibility, a Flag-tagged S581A mutant in PML-RARα (refer to S77A in RARa) and a non-related S578A mutant as a negative control, followed by Co-IP and the CHX chase in NB4 cells was constructed. Pin1 interacted with PML-RARα and its S578A mutant, which had similar protein half-lives. In contrast, the S581A mutant not only failed to interact with Pin1, but also exhibited a shorter half-life, as shown for other Pin1 substrate oncogenes (Liou et al., 2011; Lu and Zhou, 2007). Thus, Pin1 may act on PML-RARα to increase its protein stability, thereby promoting APL cell growth.

To support this idea, the effects of Pin1 KD on PML-RARα and cell growth in human APL cells by stably infecting NB4 cells with validated Pin1 shRNA lentivirus, followed by re-expressing Pin1 shRNA-resistant Pin1 or its inactive W34/K63A mutant, were examined.

FIG. 5 depicts study results 500 in which the genetic or pharmacological Pin1 ablation attenuates APL outcomes via inducing PML-RARα degradation. Results showed that Pin1 KD significantly reduced both PML-RARα protein levels and APL cell growth, both of which were fully rescued by re-constitution of shRNA-resistant Pin1, but not its inactive mutant (FIGS. 5A and 5B). Moreover, PML-RARa reduction in Pin1 KD cells was reflected by its reduced protein half-life (FIGS. 5C upper panel, and 5D). Again, reduced PML-RARα half-life was fully rescued by adding back shRNA-resistant Pin1, but not its mutant (FIGS. 5C lower panel, and 5D). Thus, Pin1 KD induces PML-RARα protein degradation and inhibits cell growth in APL cells, as does ATRA.

Figure 5A:
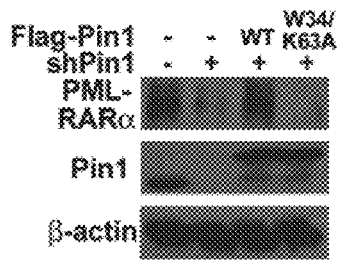
Figure 5B:
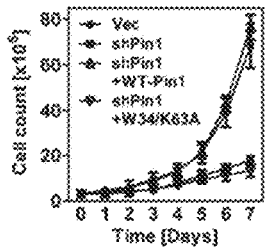
Figure 5C:
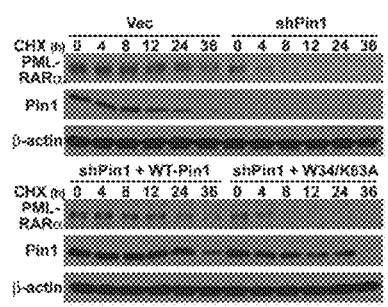
Figure 5D:
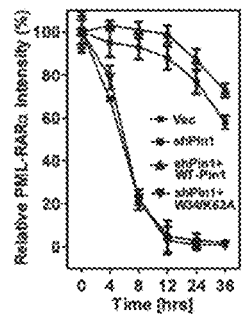
Figure 5E:
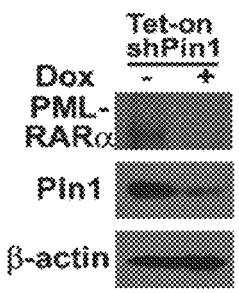
Figure 5F:
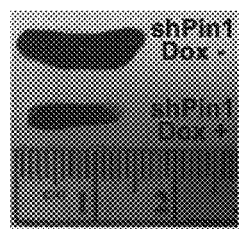
Figure 5G:
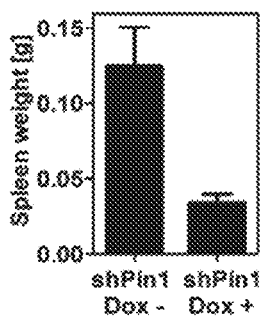
Figure 5H:
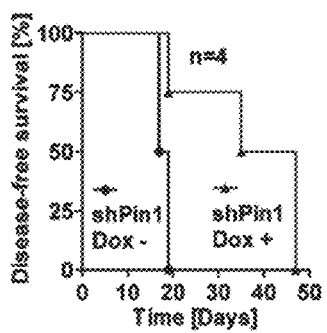
Figure 5I:
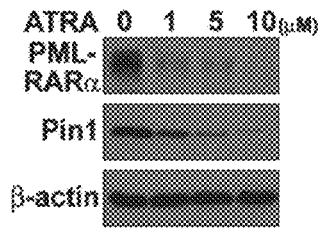
Figure 5J:

These in vitro results were further corroborated in animal studies using immunodeficient NOD-SCID-Gamma (NSG) mice transplanted with NB4 cells stably carrying an inducible Tet-on shPin1 after sublethal irradiation, as described (Gausdal et al., 2013). Doxycycline-including food was given 5 days post-transplantation throughout the course of the experiment to induce Pin1 KD, followed by monitoring of PML-RARα expression, spleen weight and overall survival. Doxycycline not only induced Pin1 KD, but also caused obvious PML-RARα degradation in the bone marrow of transplanted mice (FIG. 5E), as shown in cell cultures (FIG. 5A). Concurrently, mice fed with doxycycline-including chow displayed normal spleen size, in contrast to obvious splenomegaly in mice fed a regular chow (FIGS. 5F and 5G), which was further supported by the lack of NB4 cells in the bone marrow recognized by human CD45 antibody. More importantly, disease-free survival on doxycycline-given mice was significantly extended, compared to control mice (n=4) (FIG. 5H). Notably, Pin1 was expressed close to the normal level in one doxycycline-induced mouse that died early, in contrast to one that died later, further supporting the importance of Pin1 expression in APL. Thus inducible Pin1 KD is sufficient to cure APL phenotypes similar to ATRA, including PML-RARα degradation, spleen weight reduction and survival, supporting that the anti-leukemic effect of ATRA is in part mediated by Pin1 inhibition.

Figure 5K:
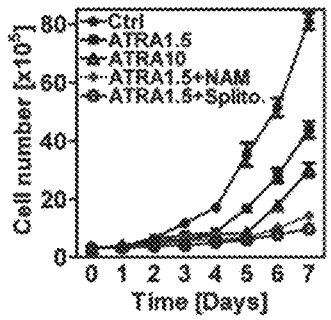

If Pin1 is a major target for ATRA to induce PML-RARα degradation, other structurally distinct Pin1 inhibitors, despite less potent and no so specific, may mimic ATRA to induce PML-RARα degradation and to treat APL phenotypes. For this purpose, three specific Pin1 inhibitors PiB, EGCG, Juglone as well as ATRA were used to treat NB4 cells. Although these compounds inhibited Pin1 without degrading it, they all induced PML-RARα degradation in a dose-dependent manner (FIGS. 5I and 5J), thus indicating that Pin1 inhibition by a total of four distinct compounds induces PML-RARa degradation, as does Pin1 KD. Next, in a consideration to test the role of activated Pin1 monomer in APL, the anti-proliferative effect of ATRA in the presence of the SIRT1 inhibitors, NAM or Splito, to deplete the monomeric Pin1 reservoir was examined. Although cell growth curve of NB4 cells in response to 1.5 µM ATRA showed less growth inhibition than that in the 10 µM ATRA group, a combination of low dose ATRA and NAM or Splito greatly potentiated the anticancer effects of low dose ATRA to superior to that from high dose ATRA (FIG. 5K).

Figure 5L:
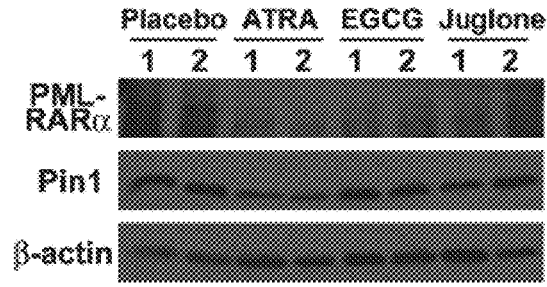
Figure 5M:
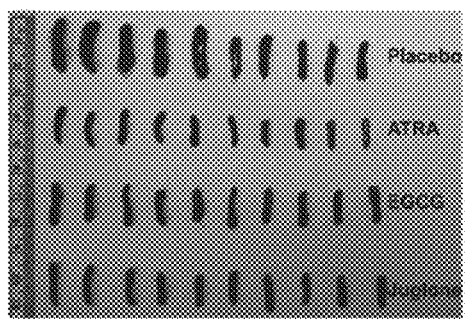
Figure 5N:
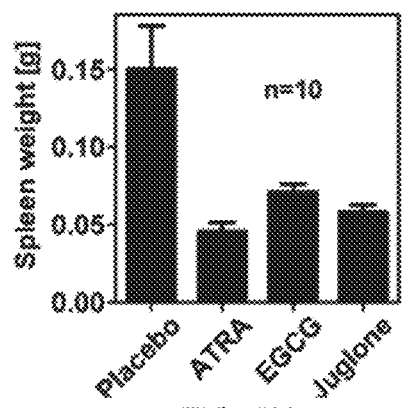

To further confirm the above in vitro results of different Pin1 inhibitors in an in situ APL mouse model, sublethal irradiated C57BL/6 mice were engrafted for 5 days with APL cells isolated from hCG-PML-RARα transgenic mice, and treated with EGCG or Juglone, in parallel with ATRA. After 20 days, mice were sacrificed to detect APL phenotypes including Pin1 and PML-RARα levels and spleen weight. As expected, ATRA, but not EGCG and Juglone, reduced Pin1 levels in the bone barrow, although the extent of the reduction was not as profoundly as in vitro APL cells, which is likely due to the fact that mouse bone marrow includes normal cells, which were insensitive to ATRA. Nevertheless, all three Pin1 inhibitors dramatically reduced PML-RARα in the bone marrow (FIG. 5L). Unlike the placebo group displayed with enlarged spleens, spleen weights in drugs-treated animals remained nearly at basal levels (FIGS. 5M and 5N). As compared with ATRA, EGCG and Juglone were less potent in reducing PML-RARα and spleen size, and treated mice were rather sick, likely due to the fact that EGCG and Juglone are non-specific Pin1 inhibitors and have other toxic effects.

ATRA for Inducing Degradation of Both Pin1 and PML-RARα in Human APL Patients

Figure 5O:
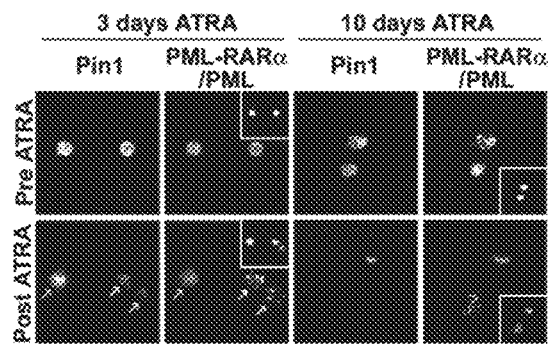
Figure 5P:
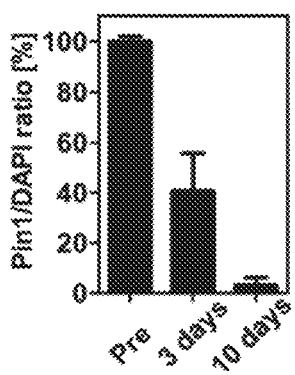
Figure 5Q:
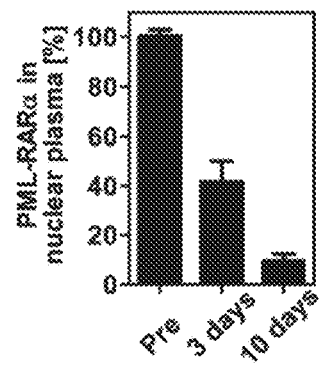

A significant question is whether ATRA treatment leads to degradation of Pin1 and PML-RARα in APL patients. To address this question, Pin1 and PML-RARα protein levels and their localization in the bone marrow of APL patients using double immunostaining with antibodies against Pin1 and PML before or after the treatment with ATRA for 3 or 10 days, were detected. Before treatment, Pin1 and PML-RARα were strikingly notable, with both being distributed to the entire nucleus in all three patients. After ATRA treatment, PML-RARα levels were significantly reduced and re-distributed to PML nuclear bodies, which it has been previously shown to represent endogenous PML protein, representing a nice indicator of ATRA response (Song et al., 2008). ATRA treatment induced a remarkable and time-dependent reduction of both Pin1 and PML-RARa. Image quantification of over 100 APL cells, with PML-RARα being roughly quantified in nuclei excluding PML bodies to avoid endogenous PML, showed that ATRA reduced both Pin1 and PML-RARα to about 40% after only 3 day of treatment (FIGS. 5O-Q). PML-RARa/PML staining pattern was tightly associated with Pin1 levels in APL cells. PML-RARa/PML was still diffusely distributed to the entire nucleus in APL cells that included more Pin1 (red arrows), but almost exclusively localized to PML bodies (likely reflecting endogenous PML) in APL cells that included much less Pin1 (yellow arrows) (FIGS. 5O-Q). After 10 days of treatment, Pin1 was reduced further to <10%, so did PML-RARα with little immunostaining signal outside of PML bodies (FIGS. 5O-Q). These results were also confirmed using human APL NB4 cells, where ATRA led to a dramatic Pin1 reduction after 4 days of treatment. Taken together, the ATRA-mediated anti-APL effects are in part mediated via ablating Pin1 to induce PML-RARa degradation, even in human APL patients.

ATRA for Breast Cancer Treatment

In one aspect of the present disclosure, description of how ATRA ablates the activated Pin1 monomer to inhibit many cancer-driving pathways at the same time in human breast cancer cells is disclosed.

Although ATRA has been approved for treating APL patients, its efficacy and drug mechanism in treating solid tumors is still being studied. Because ATRA may ablate Pin1, whose activity turns on numerous cancer-driving molecules in many solid tumors, a study verifying the ablation of the activated Pin1 monomer to inhibit many cancer-driving pathways may be conducted.

FIG. 6 illustrates study results 600 in which ATRA may have anticancer activity in other cancer types. Breast cancer was used as model due to the substantial oncogenic role of Pin1 in vitro and in vivo. The first step was to test whether ATRA may reverse the oncogenic phenotypes induced by Pin1 overexpression, including induction of centrosome amplification, activation of the cyclin D1 promoter, and enhancement of foci formation. Study results 600 indicated that Pin1 overexpression led to multiple centrosomes in about 60% cells, which however was dose-dependently and completely inhibited by ATRA as shown in FIGS. 6A and 6B. ATRA also fully inhibited the oncogenic ability of Pin1 to activate the cyclin D1 promoter (FIG. 6C) or to enhance foci formation (FIGS. 6D and 6E) in MDA-MB-231 cells in a dose-dependent manner.

Figure 6A:
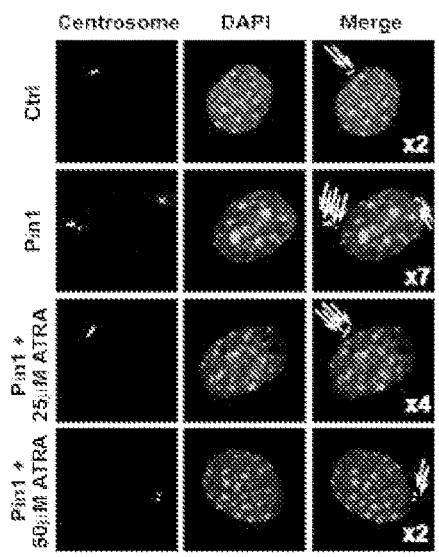
Figure 6B:
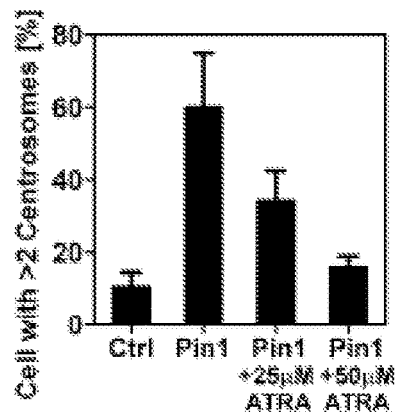
Figure 6C:
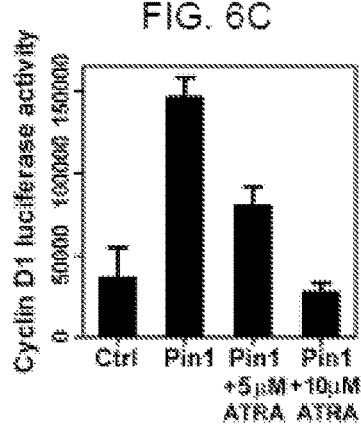
Figure 6D:
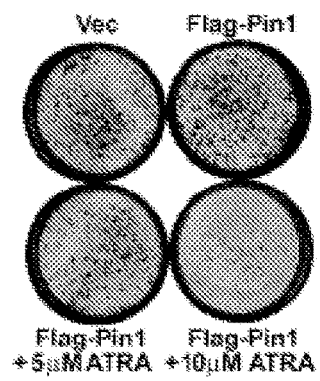
Figure 6E:
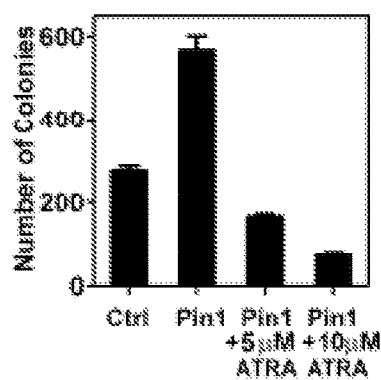
Figure 6F:
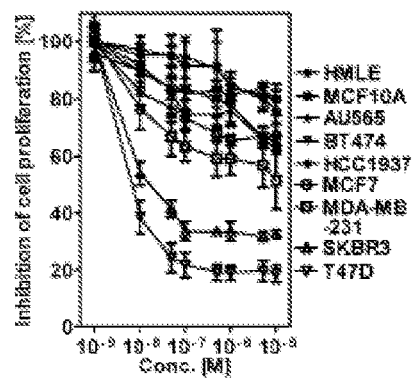
Figure 6G:
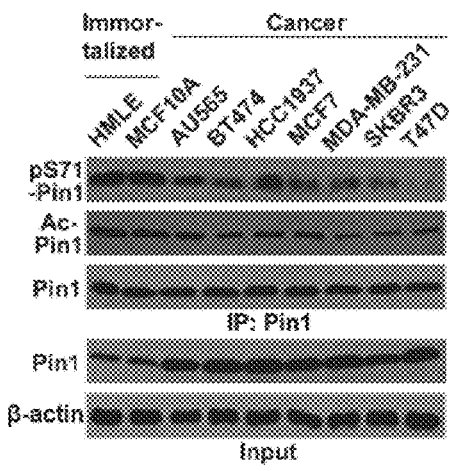

To support the inhibitory effects of ATRA on human breast cancer cell growth, ATRA was tested against 9 different human breast cancer cell lines, ranging from immortalized normal cells to malignant ones. Immortalized but non-transformed MCF10A and HMLE cells were highly resistant, but malignant cells showed different drug susceptibility to ATRA (FIG. 6F). To address ATRA sensitivity among breast cell lines, Pin1 protein levels and post-translational modifications were analyzed. As compared with normal MCF10 and HMLE cells, Pin1 was over-expressed and its acetylation was reduced in all breast cancer cells (FIG. 6G). Yet, latter results do not explain the difference in ATRA sensitivity among different cancer cell lines.

Figure 6H:
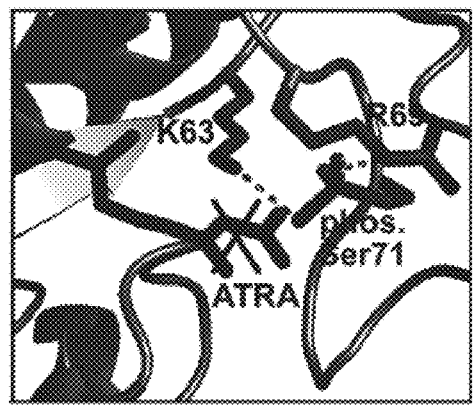

Since phosphorylation-mimicking S71E, but non-phosphorylatable S71A mutation prevented Pin1 from binding ATRA, the possibility that S71 phosphorylation would affect ATRA's sensitivity was examined. The levels of S71 phosphorylation in different cell lines were tightly correlated with ATRA's sensitivity. S71 was phosphorylated selectively in ATRA-resistant cells including HMLE, MCF10A, AU565 and HCC1937, moreover ATRA-responsive cells, T47D and SKBR3, exhibited low or nearly no detectable S71 phosphorylation (FIG. 6G). It has been previously shown that phosphorylation on S71 forms salt bridges with K63 and R69, which are the same two residues that coordinated for the binding to the carboxylic acid group of ATRA (FIG. 6H). Thus S71 phosphorylation by DAPK1 may regulate ATRA's sensitivity of cancer cells.

In order to support this possibility, it was used DAPK1 inhibition to open the ATRA-binding pocket or SIRT1 inhibition to deplete the monomeric Pin1 pool to examine whether they would increase ATRA sensitivity. Combination of ATRA with DAPK inhibitor or SIRT1 inhibitors, NAM or Splito to increase ATRA sensitivity in ATRA-resistant AU565 cells, with NAM by 2 orders of magnitude. Moreover, SIRT1 KD cells were more sensitive to growth inhibition, and Pin1 degradation induced by ATRA. These findings support the notion that ATRA selectively targets the activated Pin1 monomer.

To examine whether the inhibitory effects of ATRA on breast cancer cell growth were related to RAR activation, Ro-415253 and AC-93253 were used. As shown with APL cells, neither the pan-RARs inhibitor nor the pan-RARs activator had any obvious effects on Pin1 degradation or cell growth inhibition induced by ATRA. Thus, ATRA-mediated growth inhibition is likely via Pin1 degradation in breast cancer cells, as in APL cells.

Figure 6I:
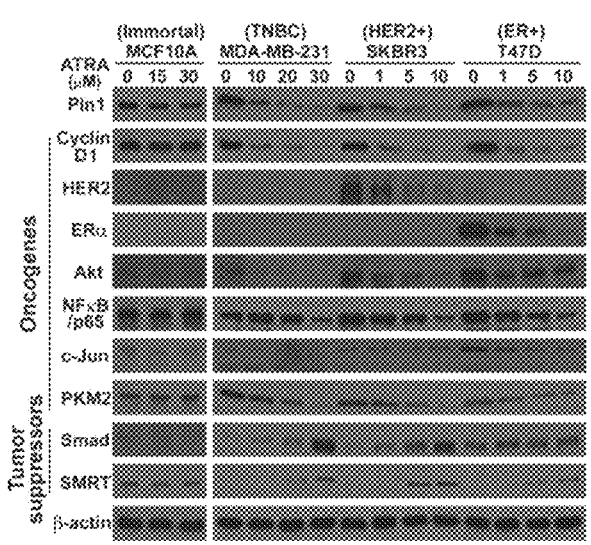
Figure 6J:
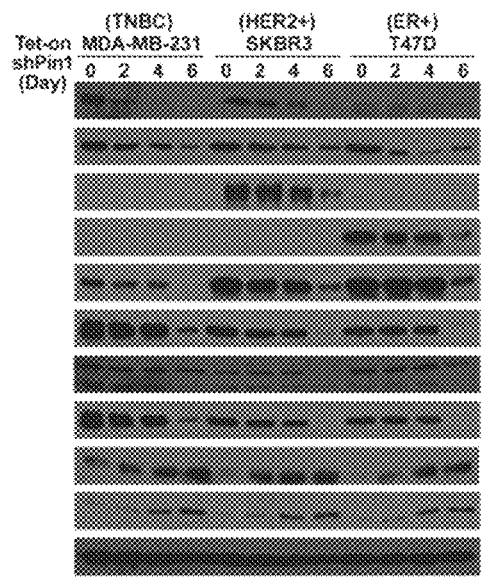
Figure 8A:
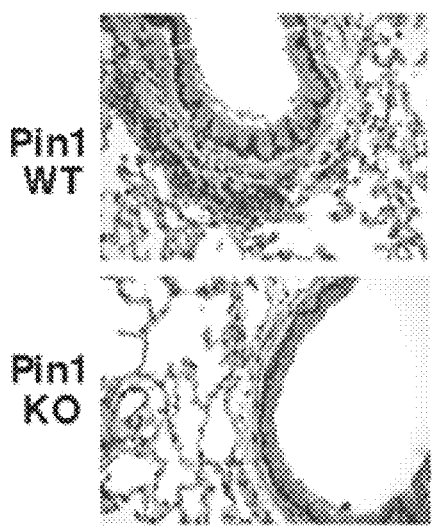
Figure 8B:
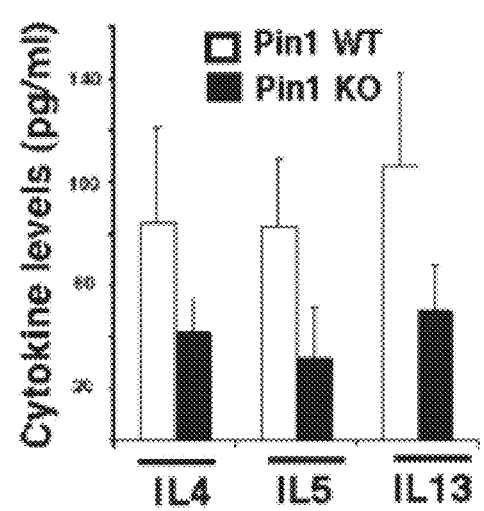
Figure 8C:
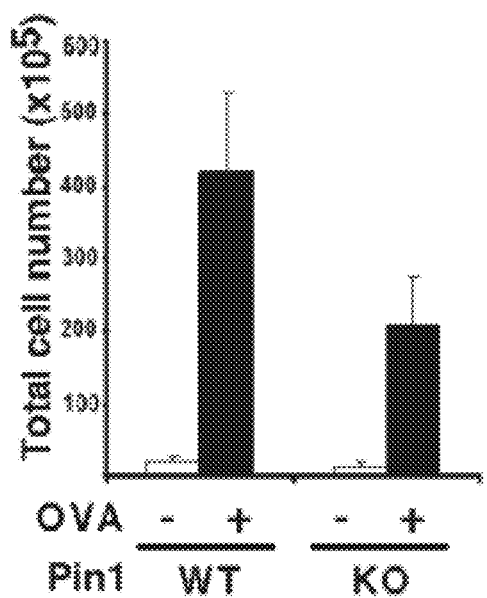
Figure 8D:
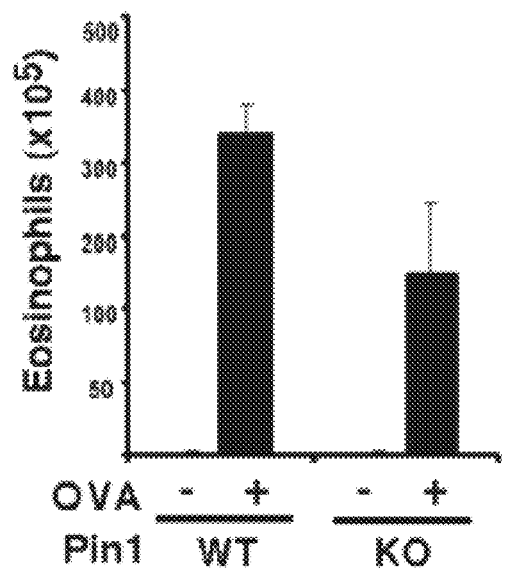

To further support that ATRA targets Pin1 in breast cancer, it was examined whether ATRA would affect protein levels of a selected set of oncogenes and tumor suppressors, whose protein stability is shown to be regulated by Pin1 in breast cancer. ATRA-induced dose-dependent protein reduction in Pin1 and many oncogenic substrates, including cyclin D1, HER2, ERα, Akt, NFkB/p65, c-Jun, and PKM2, as well as protein induction in tumor suppressor substrates, such as Smad2/3 or SMRT in all three sensitive cell lines T47D, SKBR3 or MDA-MB-231. These effects are specific because no appreciable changes in Pin1, oncogenes or tumor suppressors were noted in normal MCF10A cells (FIG. 6I). To further support that these effects of ATRA are due to Pin1 degradation, it was stably introduced tetracycline-inducible Pin1 KD into these cells. Inducible Pin1 KO produced the same effects on the oncogenes and tumor suppressors, as did ATRA (FIG. 6J). Taken together, ATRA selectively ablated activated Pin1 to inhibit many cancer-driving pathways simultaneously. Given that T47D is HER2-expressing, SKBR3 is ER-expressing and MDA-MB-231 is triple negative, ATRA-sensitive cell lines cover a wide spectrum of breast cancer categories, suggesting that ATRA is a potential therapeutic option for treating different types of breast cancers as long as Pin1 is S71 dephosphorylated and activated.

Slow-Releasing of ATRA Ablates Pin1 and Inhibits Human Triple Negative Breast Cancer Tumor Growth in Mice Even after Overexpression of Pin1 or its Cancer-Driving Mutants Given the inhibitory effects of ATRA on breast cancer cells in vitro, a critical question is whether ATRA might inhibit breast tumor growth in vivo. Then it was decided to use human triple negative breast cancer MDA-MB-231 cells in mouse xenograft models because triple negative breast cancers have the worst prognosis among all breast cancers, and the fewest treatment options (Albeck and Brugge, 2011; Foulkes et al., 2010).

FIG. 7 illustrates study results 700 in which the slow-releasing ATRA inhibits human triple negative breast cancer tumor growth in mice. In the pilot experiments, female nude mice were subcutaneously injected with MDA-MB-231 cells into the flank, followed by administering ATRA or vehicle intraperitoneally 3 times a week for 8 weeks. Although ATRA-treated mice had slightly smaller tumors than control mice, their differences were not very striking. This ATRA's modest anti-tumor activity could be due to its short half-life of less than 1 h in humans. Thus, slow-releasing ATRA pills to maintain its constant drug level in mice was used. Mice were again subcutaneously injected with MDA-MB-231 cells into the flank and implanted 1 week later with slow-releasing ATRA or placebo pills for 8 weeks. Weekly monitoring of tumor sizes showed that tumors from the mice receiving 5 or 10 mg 21 day releasing ATRA dose-dependently progressed much slower than those in the placebo group (FIGS. 7A and 7B). Tumor samples were then collected at the end and immunoblotted with antibodies against Pin1 and its target cyclin D1. Both Pin1 and cyclin D1 were dose-dependently reduced in ATRA-treated groups (FIG. 7C). These results suggest that ATRA has strong anti-tumor activity against breast cancer but only when its short half-life is overcome.

To test whether the anti-tumor activity of ATRA against breast cancer is mediated by Pin1, it is stably expressed Flag-tagged Pin1 in MDA-MB-231 cells, followed by injection into nude mice. Overexpression of Flag-Pin1 markedly increased tumor growth by 8 fold, which again was dose-dependently and effectively inhibited by ATRA (FIGS. 7D and 7E). ATRA dose-dependently reduced both endogenous and exogenous Pin1 and its target cyclin D1 (FIG. 7F). Thus anti-tumor activity of ATRA is mediated by ablating Pin1.

It was examined whether ATRA is suitable for treating tumors driven by cancer-derived monomeric Pin1 mutants given that it induces degradation of monomeric Pin1. It is stably expressed WT, Q33K or E100D Flag-Pin1 in MDA-MB-231 cells, and then treated them with ATRA. ATRA effectively induced degradation of both monomeric Pin1 mutants in a dose-dependent manner (FIG. 7G). Furthermore, ATRA also dose-dependently and effectively inhibited the ability of the Q33K or E100D Pin1 mutant to enhance foci formation in vitro, and to promote xenograft tumor growth in mice (FIGS. 7H-J). Moreover, ATRA also dose-dependently reduced both Q33K and E100D Pin1 mutants and cyclin D1 in tumors (FIG. 7K). Collectively, ATRA has potent anti-tumor activity against breast cancer driven by WT Pin1 or its cancer-derived monomeric mutants via ablating Pin1.

ATRA for Asthma Treatment

The prevalence of asthma is increasing sharply, but the therapeutic modalities remain limited. Asthma is an inflammatory disease of the airway induced by a Th2 weighted imbalance, which is regulated in different cells by signal pathways in response to various allergens. A major regulatory mechanism in these pathways is Pro-directed phosphorylation. It has been discovered that Pro-directed phosphorylation is further regulated by the unique prolyl isomerase Pin1. Notably, it has been shown that Pin1 is activated in the airway of asthma patients, and promotes asthma by acting on multiple upstream and downstream targets in the above signal pathways, thus suggesting that Pin1 is a promising new drug target in asthma.

FIG. 8 illustrates an asthma treatment 800 that may prevent or suppress asthma phenotypes by inhibiting Pin1 in mice, where aerosol liposomal ATRA or slow releasing ATRA pellets may be applied before and during IL-33.

Ovalbumin-induced (OVA) model may be implemented with dexamethasone, and Pin1 KO as positive controls. In further embodiments, other mouse models may be employed, such as BALB/c, and house dust mite (HDM), among others. In another embodiment, other sample models may be used, such as cell model, and human samples, among others.

Having established the specificity and potency of ATRA and other Pin1 inhibitors in cell cultures, ATRA and other Pin1 inhibitors were tested on well-established murine models of asthma: (i) a classical OVA sensitization and challenge protocol for asthma induction, (ii) a shorter OVA sensitization and challenge protocol of asthma, which might produce more obvious phenotypes, as shown for ST2 KO, and (iii) i.n. exposure to recombinant mIL-33 (Peprotech), HDM (Greer Laboratories) or its major allergen recombinant Der P2 (Indoor Biotechnologies), with PBS as a control.

Since Pin1 KO or NF-kB inhibition suppresses airway remodeling in the OVA-induced chronic asthma mouse model, the effects of ATRA and or other Pin1 inhibitors were examined. ATRA may be administrated as liposomal ATRA (Sigma) through respiratory aerosol or if needed, continuous time-releasing ATRA pellets (Innovative Research of America) before and during IL-33 or HDM treatment, or OVA challenge. Dexamethasone and Pin1 KO are used as positive controls. The ability of ATRA or other Pin1 inhibitors to prevent asthma development or suppress active asthma may be examined by measuring AHR in response to acetylcholine, BAL eosinophilia, mucus production, and mucoid cell hyperplasia, various cytokine levels in BAL, and serum IgE levels.

Furthermore, these reagents may determine whether Pin1 acts in the airway, thus an assay for Pin1 levels and IRAK1 activation in the airway of the treated mice was performed. Finally, ATRA has been shown to convert Th2 memory cells into Foxp3+ regulatory T cells suppressing Th2-mediated allergic asthma. A comparison of CD25+ Foxp3+ T-cells in Pin1 WT and KO mice, and in Pin1 WT mice treated with ATRA or vehicle following allergen exposure was performed to determine if the phenotype involves ATRA mediated Pin1 inhibition.

To examine the role of Pin1 on allergic asthma, the effects of Pin1 KO on OVA-induced mouse model of allergic asthma were examined. It was found that Pin1 KO inhibited Th2 cytokine secretion, lung inflammation and eosinophilia after allergen challenge (FIG. 8A-D), consistent with the findings showing the requirement of Pin1 for pulmonary eosinophilia and bronchiolar remodeling after allergen challenge.

ATRA for Lupus Treatment

In other embodiments, ATRA or ATRA-containing formulation may be employed for treatment of lupus. In order to demonstrate Pin1's role in lupus, studies with mice were performed.

Cellular and serological role of Pin1 on Systemic Lupus Erythematosus (SLE) phenotypes of lupus prone mouse models were identified. Deletion of Pin1 in the lupus-prone mice may result in suppression of lupus parameters, such as IFN-α, which is crucial for the development of disease in the MRL/lpr mice as well as IRAK1 for Sle1 and Sle3 mice. Further procedures may include the examination of cell specific contribution of Pin1 deletion to lupus phenotype using a conditional Pin1 knock out (KO). This cell-type conditional Pin1 KO model may demonstrate the relative cell specific contribution of Pin1 to the lupus phenotype, for example in B cells, T cells or DCs.

FIG. 9 shows study results 900 of the potential application of targeting Pin1 for lupus treatment in mice, where the treatment may prevent or suppress the expression of autoimmunity in B6.lpr lupus prone mice, where Pin1 is an essential regulator of TLR signaling, a pathway known to play a major role in SLE. Effects of Pin1 manipulation in SLE pathogenesis using in vivo models may be examined as shown in FIG. 9. In further embodiments, other models, such as in vitro or human, among others, may be used.

In FIG. 9, Pin1 was removed in B6.MRL/lpr mice, a lupus prone mouse model that may be homozygous for the lymphoproliferation spontaneous mutation ($Fas^{lpr}$) and may develop systemic autoimmunity, massive lymphadenopathy associated with proliferation of aberrant T cells, arthritis, and immune complex glomerulonephrosis, recapitulating many aspects of human SLE Subsequently, B6.Pin1$^{-/-}$ mice was crossed with lupus-prone mice (B6.lpr, B6.Sle1 and B6.Sle3). B6.lpr::Pin1$^{-/-}$, B6.Sle1::Pin1$^{-/-}$ and B6.Sle3::Pin1$^{-/-}$, along with control mice, were followed for about 9 to about 12 months 15 to 20 mice, each group).

Figure 9A:
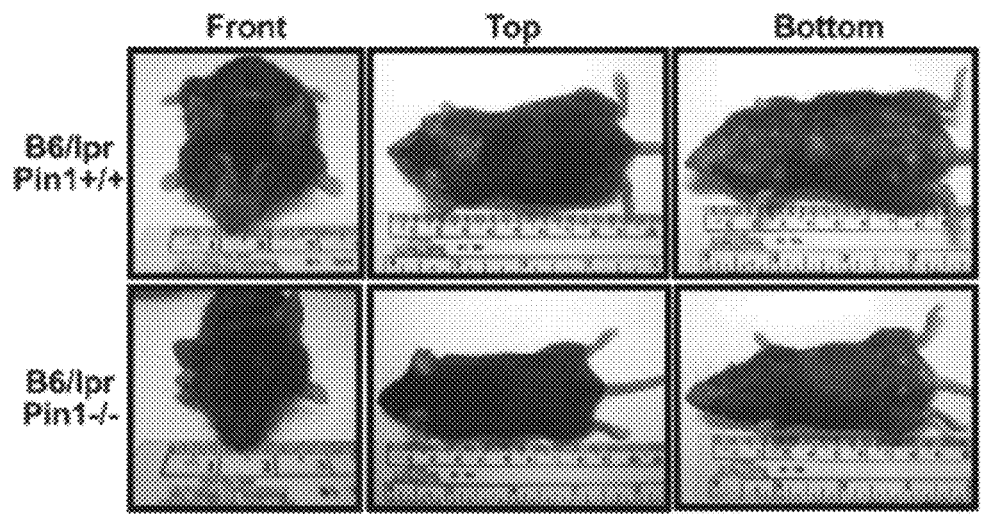
Figure 9B:
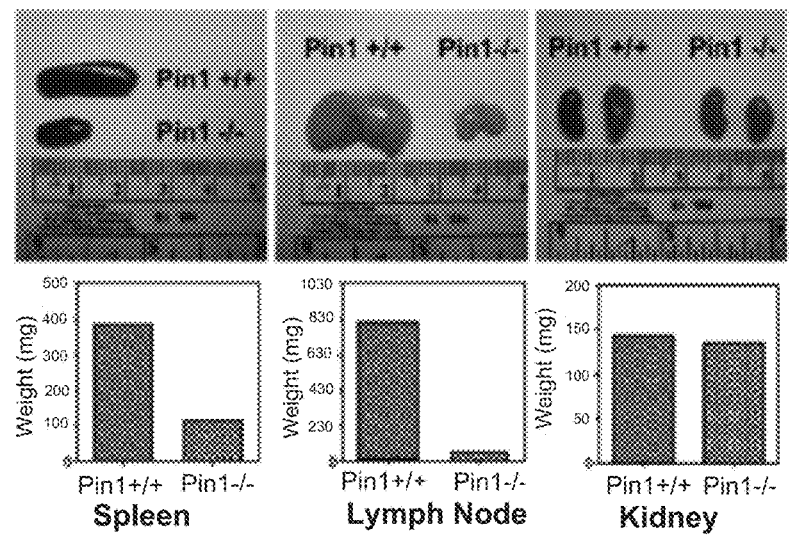
Figure 9C:
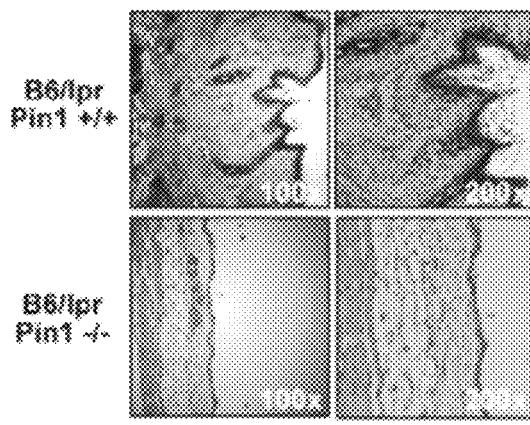
Figure 9D:
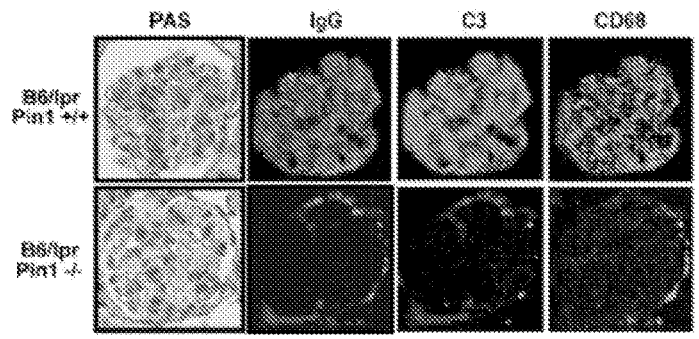
Figure 9E:
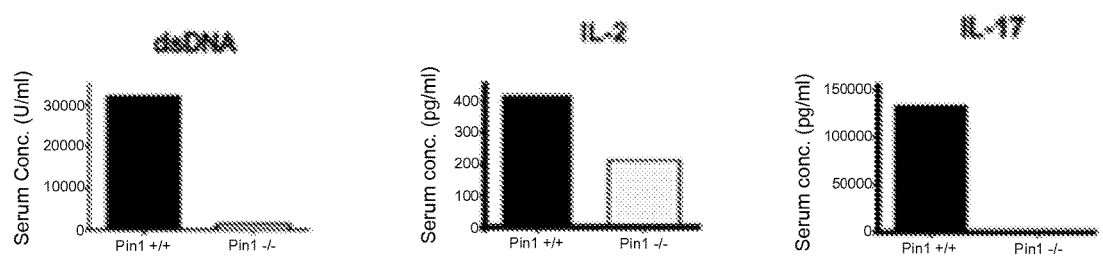
Figure 9F:
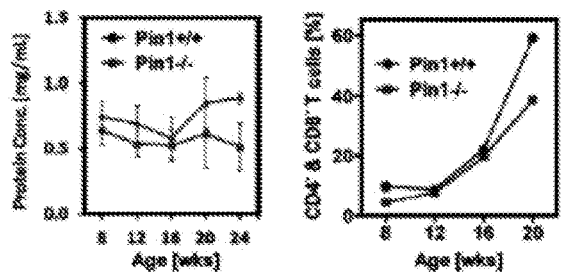

Effects of Pin1 deficiency on the lupus-related phenotypes in these mice were evaluated, including fur loss (butterfly rash area), skin inflammation, and lymphoid hyperplasia, as compared with Pin1 WT controls (FIG. 9A). Furthermore, spleen and lymph node in the B6.lpr::Pin1 KO mouse exhibited a normal size compared to those in B6.lpr::Pin1 WT mouse, which are 4 folds and 8 folds heavier in spleen and lymph node, respectively (FIG. 9B). Consequently, immunohistochemistry on the skin lesion area was performed and found that Pin1 KO mouse was fully resistant to hyperkeratinosis that occurs to Pin1 WT mouse (FIG. 9C). Although kidney sizes may be similar (FIG. 9B, right panel), renal pathological staining indicated large amount of deposition of antibody and white blood cell antigen, such as IgG, complement C3, and CD68 in the glomeruli of Pin1 WT, but not in the Pin1 KO mouse (FIG. 9D). In addition, serum biomarkers dsDNA antibody, IL-2 and IL-17 were examined, and Pin1 KO could lead to a logarithmic elimination on dsDNA antibody and IL-17 production as well as a significant reduction on IL-2 (FIG. 9E). By monthly monitoring levels of proteinuria and double negative T cell population, it was found that Pin1 KO significantly decreased both lupus markers (FIG. 9F).

FIG. 10 depicts study results 1000 in which ATRA potently suppressed the expression of autoimmunity in MRL/lpr lupus-prone mice. To test the effects of inhibiting Pin1 on lupus-related phenotypes in a mouse models, ATRA was used to treat six pairs of MRL/lpr mice at 8 weeks with the 5 mg ATRA or placebo for 8 weeks to examine whether ATRA would prevent the development of lupus-related phenotypes in this mouse model, which usually occur at 12 weeks. It was strikingly observed that ATRA drastically suppressed visual lupus-related phenotypes in all six treated mice, including fur loss (butterfly rash area), skin inflammation, and lymphoid hyperplasia, as compared with placebo-treated controls (FIG. 10A). A pair of 14 week-old ATRA-treated and placebo-treated mice were sacrificed. Spleen and lymph node in the ATRA-treated mouse exhibited normal size, but placebo-treated mouse spleen and lymph node was 2-4 fold heavier (FIG. 10B). ATRA treatment also potently inhibited hyperkeratinosis (FIG. 10C) and glomerular deposition of IgG, C3, and CD68 (FIG. 10D). These results strongly suggest that Pin1 inhibitors such as ATRA may have beneficial clinical efficacy in treating lupus.

ATRA for Treating Cocaine Addiction

In other embodiments, ATRA or ATRA-containing formulation may be employed for treatment of cocaine addiction. In order to demonstrate Pin1's role in cocaine addiction, studies with mice were performed (Park et al., 2013).

Dopamine receptor and group I mGluR signaling may be cofunctional, and MAP Kinase phosphorylates mGluR5 (S1126) within the sequence that is bound by Homer (TPPSPF). D1 dopamine receptors activate MAP Kinase, and phosphorylation of mGluR5(S1126) increasing Homer binding avidity and influences mGluR signaling. In addition, phosphorylation of mGluR5(S1126) also creates a binding site for the prolyl isomerase Pin1, where Pin1 accelerates rotation of the phosphorylated S/T-P bond in target proteins, and acts as a molecular switch. It is believed that Pin1 may be co-functional with Homer in controlling mGluR1/5 signaling.

It has been demonstrated that Pin1 catalyzes isomerization of phosphorylated mGluR5 at the $pS^{1126}$-P site and consequently enhances mGluR5-dependent gating of NMDA receptor channels. The immediate early gene (IEG) Homer1a, induced in response to neuronal activity, plays an essential role by interrupting Homer cross-linking and therefore facilitating Pin1 catalysis. Mutant mice that constrain Pin1-dependent mGluR5 signaling fail to exhibit normal motor sensitization, implicating this mechanism in cocaine-induced behavioral adaptation. Subsequently, in vivo studies confirmed that Pin1 co-immunoprecipitates with mGluR5 from mouse brain. Consistent with the notion that cross-linking Homer proteins compete with Pin1 for mGluR5 binding, Pin1 co-immunoprecipitation with mGluR5 increased in brains of mice lacking Homer (Homer1−/−Homer2−/−Homer3−/−, Homer triple knockout, HTKO), and increased in parallel with mGluR5(S1126) phosphorylation induced by acute administration of cocaine. An increase of Pin1 binding in WT mice was not detected. This could challenge the notion that Pin1 is a natural signaling partner of mGluR5(S1126), but since Homer1a protein levels in vivo are many fold less than constitutively expressed Homer proteins, the possibility that effects of Homer1a may be restricted to a minority of mGluR5(S1126) that are not easily detected in biochemical assays was considered. Overall, the data indicate that the IEG isoform Homer1a facilitates the binding of Pin1 to mGluR5 that has been phosphorylated in response to cocaine and/or dopamine receptor stimulation (Park et al., 2013).

While various aspects and embodiments have been disclosed, other aspects and embodiments are contemplated. The various aspects and embodiments disclosed are for purposes of illustration and are not intended to be limiting, with the true scope and spirit being indicated by the following claims.

The invention claimed is:

1. A pharmaceutical composition comprising a retinoid, wherein said composition is formulated for long-term delivery of said retinoid after injection of said composition into a subject.

2. The pharmaceutical composition of claim 1, wherein said composition is formulated as an injectable depot system, an injectable drug suspension, an injectable microsphere, or an injectable gel.

3. The pharmaceutical composition of claim 2, wherein said injectable drug suspension is an oil-based suspension.

4. The pharmaceutical composition of claim 2, wherein said composition is formulated for intravenous injection or intramuscular injection.

5. The pharmaceutical composition of claim 4, wherein said composition is formulated as an injectable gel and for intramuscular injection.

6. The pharmaceutical composition of claim 5, wherein said injectable gel remains in the muscle for at least 4-6 weeks after injection.

7. The pharmaceutical composition of claim 1, wherein said composition is formulated to delay the metabolism of said retinoid.

8. The pharmaceutical composition of claim 7, wherein said composition comprises one or more liposomes comprising said retinoid.

9. The pharmaceutical composition of claim 1, further comprising a pharmaceutically acceptable excipient.

10. The pharmaceutical composition of claim 1, wherein said retinoid is all-trans retinoic acid.

11. A method of treating a Pin1-related disorder in a subject in need thereof, comprising administering the composition of claim 1 to said subject.

12. The method of claim 11, wherein said Pin1-related disorder is a cancer, an immune disorder, or cocaine addiction.

13. The method of claim 12, wherein said cancer is selected from the group consisting of: acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia, Hodgkin's disease, non-Hodgkin's disease, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, esophageal cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma.

14. The method of claim 13, wherein said cancer is breast cancer.

15. The method of claim 12, wherein said immune disorder is asthma or lupus.

16. The method of claim 11, wherein said subject is determined to have elevated levels of a Pin1 marker prior to said administration.

17. The method of claim 11, further comprising administering a second therapeutic compound.

18. The method of claim 17, wherein said second therapeutic compound is chemotherapeutic compound, a DAPK inhibitor, a SIRT1 inhibitor, a deacetylase inhibitor, a second Pin1 inhibitor, a Plk1 inhibitor, an anti-inflammatory compound, an antimicrobial compound, an antiviral compound, or any combination thereof.

19. The method of claim 17, wherein said composition and said second therapeutic compound are administered separately or in a single formulation.

\* \* \* \* \*

UNITED STATES PATENT AND TRADEMARK OFFICE
CERTIFICATE OF CORRECTION

PATENT NO. : 9,968,579 B2
APPLICATION NO. : 15/326979
DATED : May 15, 2018
INVENTOR(S) : Kun Ping Lu et al.

It is certified that error appears in the above-identified patent and that said Letters Patent is hereby corrected as shown below:

On the Title Page

Under Assignee, replace "Isreal" with --Israel--;
Under (*) Notice, replace "by 0 days. days" with --by 0 days.--;
Under (74) Attorney, Agent, or Firm, replace "Elhing" with --Elbing--;
Under ABSTRACT, replace "PML-RARa" with --PML-RARα--.

In the Drawings

Figure 10A:
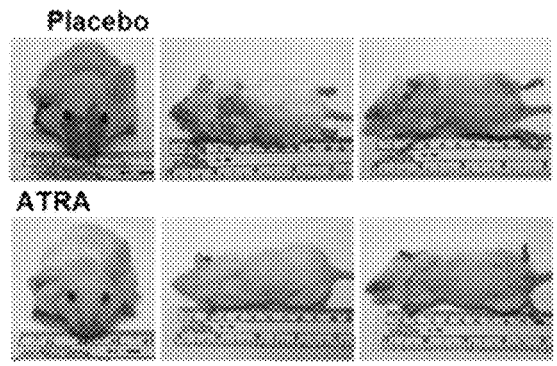
Figure 10B:
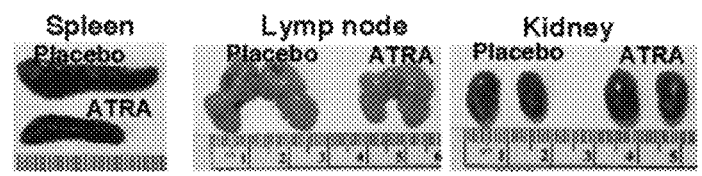
Figure 10B:
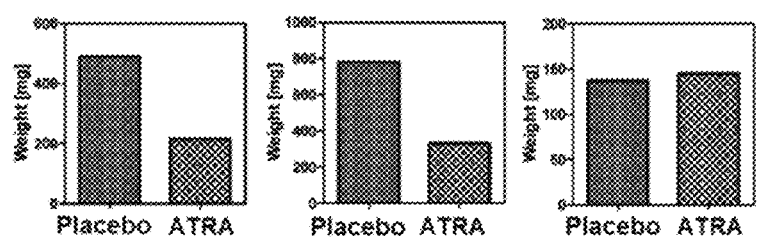
Figure 10C:
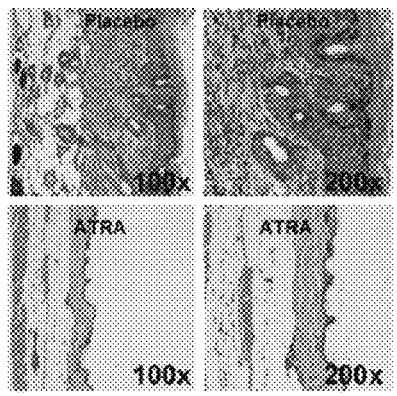
Figure 10D:
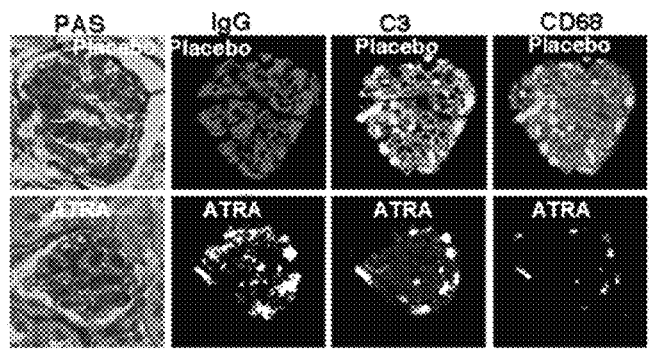

Sheet 14, in FIG. 10B, replace "Lymp node" with --Lymph node--.

In the Specification

Column 3, Line 6, replace "PML-RARa" with --PML-RARα--;
    Line 40, replace "the inactivate Pin1 dimer" with --the inactivated Pin1 dimer--;
    Line 64, replace "PML-RARa" with --PML-RARα--;
    Line 66, replace "PML-RARa" with --PML-RARα--.

Column 4, Line 31, replace "desumolation" with --desumoylation--.

Column 5, Line 38, replace "deactylase" with --deacetylase--;
    Line 21, replace "oligodenroglioma" with --oligodendroglioma--.

Column 6, Line 57, replace "PML-RARa" with --PML-RARα--;
    Line 59, replace "PML-RARa" with --PML-RARα--;
    Line 64, replace "PML-RARa" with --PML-RARα--.

Column 7, Line 2, replace "PML-RARa" with --PML-RARα--;
    Lines 6-7, replace "PML-RARa" with --PML-RARα--;
    Line 14, replace "PML-RARa" with --PML-RARα--;

Signed and Sealed this
Sixth Day of April, 2021

Drew Hirshfeld
*Performing the Functions and Duties of the
Under Secretary of Commerce for Intellectual Property and
Director of the United States Patent and Trademark Office*

Line 16, replace "PML-RARa" with --PML-RARα--;
Line 22, replace "PML-RARa" with --PML-RARα--;
Lines 24-25, replace "hCG-PML-RARa" with --hCG-PML-RARα--;
Line 27, replace "PML-RARa" with --PML-RARα--;
Line 30, replace "PML-RARa" with --PML-RARα--;
Lines 36-37, replace "treatment (0). Note," with --treatment (O). Note,--.

Column 11, Line 15, replace "phosphoserinelthreonine-proline" with
--phosphoserine/threonine-proline--;
Line 62, replace "RARa" with --RARα--.

Column 12, Line 30, replace "promyeiocytic" with --promyelocytic--.

Column 13, Line 28-29, replace "oligodenroglioma" with --oligodendroglioma--;
Lines 46-47, replace "anti-anti-inflammatory" with --anti-inflammatory--.

Column 14, Line 21, replace "gentuzumab" with --gemtuzumab--;
Line 23, replace "melphalen" with --melphalan--.

Column 15, Line 39, replace "(FIG. 10)" with --(FIG. 1D)--.

Column 18, Line 21, replace "RARa" with --RARα--;
Line 26, replace "RARa" with --RARα--;
Lines 47-48, replace "PML-RARa" with --PML-RARα--.

Column 19, Line 24, replace "PML-RARa" with --PML-RARα--.

Column 20, Line 4, replace "PML-RARa" with --PML-RARα--;
Line 9, replace "PML-RARa/PML" with --PML-RARα/PML--;
Lines 10-11, replace "PML-RARa/PML" with --PML-RARα/PML--;
Line 22, replace "PML-RARa" with --PML-RARα--.

In the Claims

Column 26, Line 49, Claim 13 replace "oligodenroglioma" with --oligodendroglioma--;
Line 63, Claim 18 replace "compound is chemotherapeutic" with --compound is a chemotherapeutic--.